United States Patent
Alfareed et al.

(10) Patent No.: US 12,357,583 B2
(45) Date of Patent: Jul. 15, 2025

(54) MAGNETOELECTRIC NANOCOMPOSITES AND METHOD OF PREPARATION THEREOF

(71) Applicant: Imam Abdulrahman Bin Faisal University, Dammam (SA)

(72) Inventors: Tahani Mohammed Alfareed, Dammam (SA); Munirah Abdullah Almessiere, Dammam (SA); Yassine Slimani, Dammam (SA); Firdos Alam Khan, Dammam (SA); Ebtesam Abdullah Al-Suhaimi, Dammam (SA); Abdulhadi Baykal, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 147 days.

(21) Appl. No.: 17/701,110

(22) Filed: Mar. 22, 2022

(65) Prior Publication Data

US 2023/0320997 A1    Oct. 12, 2023

(51) Int. Cl.
| | | |
|---|---|---|
| A61K 9/51 | (2006.01) | |
| A61K 45/06 | (2006.01) | |
| B82Y 5/00 | (2011.01) | |
| B82Y 30/00 | (2011.01) | |
| B82Y 40/00 | (2011.01) | |

(52) U.S. Cl.
CPC ............ *A61K 9/5192* (2013.01); *A61K 45/06* (2013.01); *B82Y 5/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| | | |
|---|---|---|
| 9,724,503 B2 | 8/2017 | Khizroev |
| 1,035,487 A1 | 7/2019 | Liang |
| 2018/0297858 A1 | 10/2018 | Betal et al. |
| 2022/0139600 A1* | 5/2022 | Zehani ............. C01G 51/006 424/647 |

FOREIGN PATENT DOCUMENTS

CN    112043682 A    12/2020

OTHER PUBLICATIONS

Yousaf et al. (Structural, magnetic, and electrical evaluations of rare earth Gd3+ doped in mixed Co—Mn spinel ferrite nanoparticles, Ceramics International, 2021). (Year: 2021).*
Andronescu et al. (Photoluminescent Hydroxylapatite: Eu3+ Doping Effect on Biological Behavior, Nanomaterials (Basel), 2019) (Year: 2019).*
Effect of europium doping on the microstructural, optical and photocatalytic properties of ZnO nanopowders, Arab Journal of Basic and Applied Sciences, 2021 (Year: 2021).*
Shahzad et al. (Field-controlled magnetoelectric core-shell CoFe2O4@BaTiO3 nanoparticles as effective drug carriers and drug release in vitro, Materials Science & Engineering C, 2021). (Year: 2021).*
Almessiere et al. (Correlation between microstructure parameters and anti-cancer activity of the [Mn0.5Zn0.5](EuxNdxFe2-2x)O4 nanoferrites produced by modified sol-gel and ultrasonic methods, Ceramics International, 2020). (Year: 2020).*
Parida, et al. ; Magnetic and magnetoelectric response of Gd doped nickel ferrite and barium titanate nanocomposite ; Journal of Applied Physics, vol. 127, Issue 11 ; Mar. 18, 2020.
Rodzinski, et al. ; Targeted and controlled anticancer drug delivery and release with magnetoelectric nanoparticles ; Scientific Reports ; Feb. 15, 2016.
Rather, et al. ; Particles maultiferroic Ba0.99Tb0.02Ti0.99O3—CoFe1.8Mn0.2)4 composites: Improved dielectric ferroelectric and magneto-dielectric properties ; Journal of Alloys and Compounds, vol. 887 ; Dec. 20, 2021.

* cited by examiner

*Primary Examiner* — Andrew S Rosenthal
*Assistant Examiner* — Danielle Kim
(74) *Attorney, Agent, or Firm* — Oblon, McClelland, Maier & Neustadt, L.L.P.

(57) ABSTRACT

A magnetoelectric nanocomposite (MEN) is described. The MEN are used as a colorectal cancer treatment. The MEN includes a shell having at least one ferroelectric compound and a rare earth (R) metal doped spinel ferrite nanoparticle (SFNP) core, of a formula of $Co_xMn_{1-x}R_{2-y}Fe_yO_z$ wherein x=0.1-0.9, y=1.90-1.99, and z=3-5; and R is at least one rare earth metal selected from the group consisting of cerium (Ce), europium (Eu), gadolinium (Gd), terbium (Tb) and thulium (Tm). A method of making MENs is also provided.

7 Claims, 19 Drawing Sheets

MAGNETOELECTRIC NANOCOMPOSITES AND METHOD OF PREPARATION THEREOF

BACKGROUND

Technical Field

The present disclosure is directed to a nanocomposite, and particularly to a magnetoelectric nanocomposite (MEN), a method of preparing the MEN, and methods of treating cancer by administering the MEN to a patient having a cancer.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present disclosure.

In recent years, magnetoelectric nanocomposites (MENs) have received great attention in the biomedical area owing to their unique intrinsic properties. MENs are characterized by site-specific delivery of small molecules, on-demand release, wireless sensing, and electric field controlling at the nanoscale. MENs are a combination of ferroelectric and ferromagnetic phases that provide magnetoelectric (ME) duality and functionality that may not exist in either material alone. One of the most attractive applications of MENs is magnetically assisted in vivo targeted and controlled drug delivery. The MENs have a drug associated thereto, and navigate throughout the body and are localized at a specific destination with the aid of an external magnetic field. In other words, they function as a drug delivery vehicle or a system to deliver the drug at the desired destination. Although numerous MENs are known in the art, there still is a compromise between the specificity, bioavailability and controlled drug release. Therefore, there exists a need to develop MENs which may substantially reduce or eliminate the above limitations.

SUMMARY

In an exemplary embodiment, a rare earth metal doped spinel ferrite nanoparticle (SFNP) is described. The SFNP has a formula of $Co_xMn_{1-x}R_{2-y}Fe_yO_z$ where x=0.1-0.9, y=1.90-1.99, and z=3-5. R in said formula is at least one rare earth metal selected from the group consisting of cerium (Ce), europium (Eu), gadolinium (Gd), terbium (Tb) and thulium (Tm).

In some embodiments, the rare earth metal doped SFNP has an average crystallite size of 20-30 nanometers (nm).

In an exemplary embodiment, a colorectal cancer treating composition is described. In an embodiment, the colorectal cancer treating composition includes the rare earth doped SFNP selective for human colorectal carcinoma (HCT)-116 cells.

In some embodiments, the colorectal cancer treating composition including the rare earth metal doped SFNP has a concentration of 1300-1500 micrograms per milliliter (µg/mL).

In some embodiments, the colorectal cancer treating composition including the rare earth metal doped SFNP further includes an anti-cancer drug associated to the rare earth metal doped SFNP.

In yet another exemplary embodiment, a method of treating colorectal cancer in a subject is described. The method includes administering to a subject the rare earth metal doped SFNP in an amount effective to decrease the average cancer cell viability of a cancer by more than 10%.

In another exemplary embodiment, a magnetoelectric nanocomposite (MEN) is described. The MENs include a shell having at least one ferroelectric compound, and the SFNP core. The SFNP core has a formula of $Co_xMn_{1-x}R_{2-y}Fe_yO_z$ where x=0.1-0.9, y=1.90-1.99, and z=3-5, where R is at least one rare earth metal selected from the group consisting of Ce, Eu, Gd, Tb and Tm.

In some embodiments, the ferroelectric compound is barium titanate (BTO).

In some embodiments, the MENs have a substantially spherical shape, and an average size of 5-30 nanometers (nm), where the spheres are agglomerated to form aggregates with an average size of 50-500 nm.

In some embodiments, the MEN has an average crystallite size of 30-45 nm.

In some embodiments, the MEN includes 27-33 percentage weight (wt. %) barium (Ba), 10-12 wt. % titanium (Ti), 5-15 wt. % cobalt (Co), 3-6 wt. % manganese (Mn), 0.5-1 wt. % R (rare earth metals), 21-25 wt. % iron (Fe), and 18-24 wt. % oxygen (O). The wt. % is based on the total weight of the Ba, Ti, Co, Mn, R, Fe, and O in the MENs.

In some embodiments, the MEN has a magnetoelectric coefficient of 12-25 millivolt per centimeter oersted (mV/cm Oe) at 1800 Oe.

In some embodiments, the MEN has a zeta potential of −17 to 13 mV.

In another exemplary embodiment, a method of making the MENs is described. The method includes making the rare earth metal doped SFNP core by forming a mixture of at least one iron (III) salt, at least one cobalt (II) salt, and at least one manganese (II) salt in water, dissolving at least one rare earth metal salt from the group consisting of Ce, Eu, Gd, Tb, and Tm in acid at a temperature greater than 150° C. for at least 1 hour to form a dissolved rare earth metal solution, adjusting the pH of the dissolved rare earth metal solution to at least 10 with a base to form an adjusted dissolved rare earth metal solution, combining the mixture and the adjusted dissolved rare earth metal solution to form a synthetic solution, subjecting the synthetic solution to ultrasonic irradiation with a power of at least 50 watt (W) and a frequency of at least 10 kilohertz (KHz) for at least 1 hour to form a precipitate, washing the precipitate with water and drying at a temperature greater than 150 degree centigrade (° C.) for at least 8 hours to get a dried material, and pulverizing the dried material to obtain a rare earth metal doped SFNP core. The method further includes making a shell material solution by mixing the ferroelectric compound in an acid and heating for at least 10 minutes at the temperature greater than 50° C. to form the shell compound solution. Furthermore, the method includes sonicating the rare earth metal doped SFNP core in a protic solvent for at least 10 minutes to form a suspension, and forming a second mixture of the suspension with the shell compound solution and sonicating for at least 2 hours at the temperature greater than 50° C. The method further includes heating the second mixture to at least 100° C. to form a powder, followed by grinding the powder and calcining at the temperature greater than 500° C. to obtain the MEN.

In some embodiments, the MEN is non-toxic to human embryonic kidney (HEK)-293 cells at a concentration of 1300-1500 µg/mL.

In an exemplary embodiment, a colorectal cancer treating composition is described. The colorectal cancer treating composition includes the MEN, where the MEN is selective for HCT-116 cells.

In some embodiments, the colorectal cancer treating composition includes the MEN, and the colorectal cancer treating composition has a concentration of 1300-1500 µg/mL.

In some embodiments, the colorectal cancer treating composition includes the MEN, and an anti-cancer drug associated to the MEN.

In an exemplary embodiment, a method of treating the colorectal cancer in the subject is described. The method includes administering to the subject the MEN in an amount effective to decrease the average cancer cell viability of the cancer by more than 10%.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
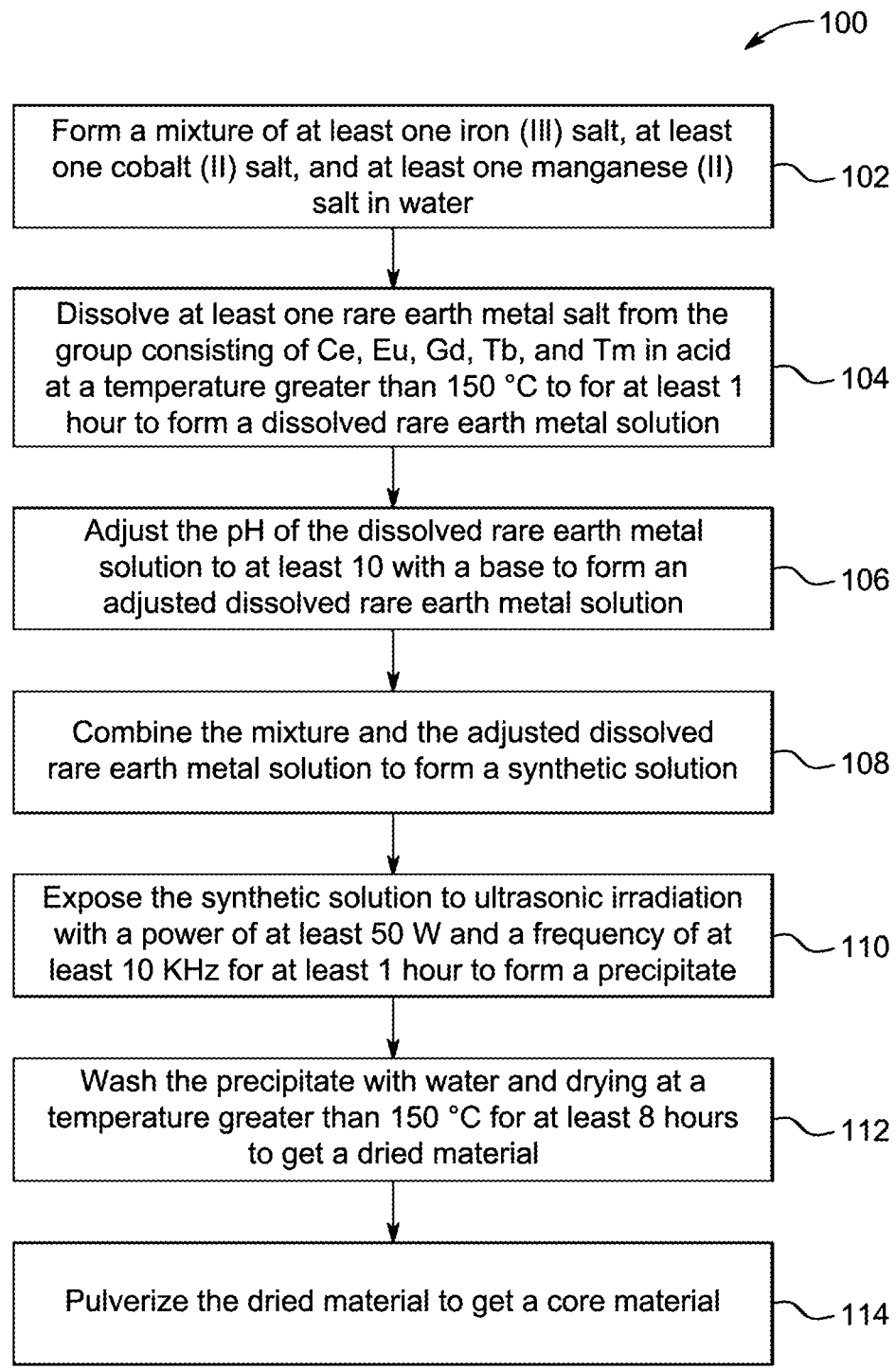
FIG. 1 is a schematic flow diagram of a method of forming a rare earth metal doped SFNP core, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

As used herein, the term "rare earth metal" refers to a group of 15 elements referred to as the lanthanide series in the periodic table of elements.

As used herein, the term "doping" refers to the intentional introduction of impurities into an intrinsic semiconductor for the purpose of modulating its electrical, optical and structural properties.

As used herein, the term "nanoparticle" refers to a small particle that ranges between 1 to 1,000 nanometers in size.

As used herein, the term "spinel ferrite" refers to a complex oxide crystal structure with a face-centered cubic core and a unit formula of $AFe_2O_4$.

As used herein, the term "colorectal cancer" refers to the cancer of colon or the rectum.

As used herein, the term "anti-cancer drug" refers to any drug that is effective in the treatment of malignant, or cancerous, disease.

As used herein, the term "ferroelectric compound" refers to compounds having a spontaneous electric polarization that can be reversed by the application of an external electric field.

As used herein, the term "nanocomposite" refers to a multiphase solid material where one of the phases has one, two or three dimensions of less than 1,000 nanometers (nm) or structures having nano-scale repeat distances between the different phases that make up the material.

As used herein, the term "magnetoelectric" refers to the interaction between the magnetic and electric subsystems in a given material.

As used herein, the term "magnetoelectric coefficient" refers to the most critical indicator for the magnetoelectric coupling properties in multiferroic materials.

As used herein, the term "zeta potential" refers to a physical property which is exhibited by any particle in suspension, macromolecule or material surface.

As used herein, the term "HCT-116 cells" or "human colorectal cancer 116 cells" refer to cell line that was isolated from the colon of an adult male, colon cancer patient.

As used herein, the term "HEK-293 cells" or "human embryonic kidney 293" refers to a specific immortalized cell line derived from a spontaneously miscarried or aborted fetus or HEK cells grown in tissue culture taken from a female fetus in 1973.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

Embodiments of the present disclosure are directed to a magnetoelectric nanocomposite (MEN) for use as an anti-cancer composition, and drug delivery system for treatment of colorectal cancer. The MENs of the present disclosure possess biocompatibility, high structural stability as well as dual physical and biological properties (ferroelectric and ferromagnetic), (anticancer drug and nanocarrier) in a single phase, respectively. Although the description herein provided is the use of MENs for treatment of colorectal cancer, aspects of the present disclosure can be used for treatment of other cancers as well. Aspects of the present disclosure are also directed to a method of preparing rare-earth (R) doped CoMnRFe (R=Ce, Eu, Gd, Tb, and Tm) spinel ferrites and further coating them with $BaTiO_3$ (BTO) by combining sonochemical and sol-gel methods, to prepare core-shell CoMnRFe@BTO (R=Ce, Eu, Gd, Tb, and Tm) MENs.

Biological influences of the MENs of the present disclosure CoMnRFe@BTO MENs (R=Ce, Eu, Gd, Tb, and Tm) on human colorectal carcinoma cells (HCT)-116 demonstrate a strong inhibitory effect against the tumor cells in concentration dependent manner.

In an embodiment, a rare earth metal doped spinel ferrite nanoparticle (SFNP) is described. The SFNP has a formula of $Co_xMn_{1-x}R_{2-y}Fe_yO_z$ wherein x=0.1-0.9, y=1.90-1.99, and z=3-5; where R is at least one rare earth metal selected from the group consisting of Ce, Eu, Gd, Tb, and Tm. In some embodiments, SFNP has an average crystallite size is 20-30 nanometers (nm), preferably 22-28 nm, or 24-26 nm.

An effective amount of SFNP is used for treating a colorectal cancer, where the rare earth doped SFNP are selective for HCT-116 cells. In some embodiments, composition of SFNP have a concentration of 1300-1500 µg/mL to inhibit a growth of HCT-116 cells by at least 10%, preferably 20%, 30%, or all HCT-116 cells. Effective amount refers to a dose or concentration of a drug that produces a biological response. Herein the biological response refers to a decrease in cell viability following treatment with the nanoparticles. The cell viability is the percentage of cells that survive following exposure to the nanoparticles. Some embodiments include administering to the subject the rare earth metal doped SFNP in an amount effective to decrease the average cancer cell viability of the cancer by more than 10%, preferably 20%, 30% or decrease all cancer cell viability. In the present embodiment, the subject is a human. In some embodiments, the subject may be an animal.

In some embodiments, the colorectal cancer treatment includes an anti-cancer drug, where the anti-cancer drug is associated to the rare earth metal doped SFNP. In some embodiments the association may be through an ionic bond and/or covalent bond. In an embodiment, the anti-cancer drug associated to the SFNP is administered to a patient and a magnetic field is applied to the exterior of the patient to navigate the drug to a desired part of the patient body. In an embodiment the anti-cancer drug is any pharmaceutical compound for treating colorectal cancer known in the art.

A magnetoelectric nanocomposite (MEN) includes a shell comprising at least one ferroelectric compound, and the rare earth metal doped spinel ferrite nanoparticle (SFNP) core, having a formula of $Co_xMn_{1-x}R_{2-y}Fe_yO_z$ wherein x=0.1-0.9, y=1.90-1.99, and z=3-5, where R is at least one rare earth metal selected from the group consisting of Ce, Eu, Gd, Tb and Tm. In an embodiment, the ferroelectric compound is selected from the group consisting of lead titanate, lead zirconate titanate, and barium titanate. In some embodiments, a ferroelectric compound is barium titanate (BTO). In another embodiment, MENs include 27-33 wt. % barium (Ba), preferably 28-32, or 29-30 wt. % Ba, 10-12 wt. % titanium (Ti), preferably 10.5-11.5, or 10.8-11.2 wt. % Ti, 5-15 wt. % cobalt (Co), preferably 7-12, or 9-10 wt. % Co, 3-6 wt. % manganese (Mn), preferably 3.5-5.5, or 4-5 wt. % Mn, 0.5-1 wt. % rare earth metal (R), preferably 0.6-0.9, or 0.7-0.8 wt. % R, 21-25 wt. % iron (Fe), preferably 22-24, or 22.5-23 wt. % Fe, and 18-24 wt. % oxygen (O), preferably 19-23, or 20-22 wt. % O, based on the total weight of the Ba, Ti, Co, Mn, R, Fe, and O in MEN.

Figure 4:
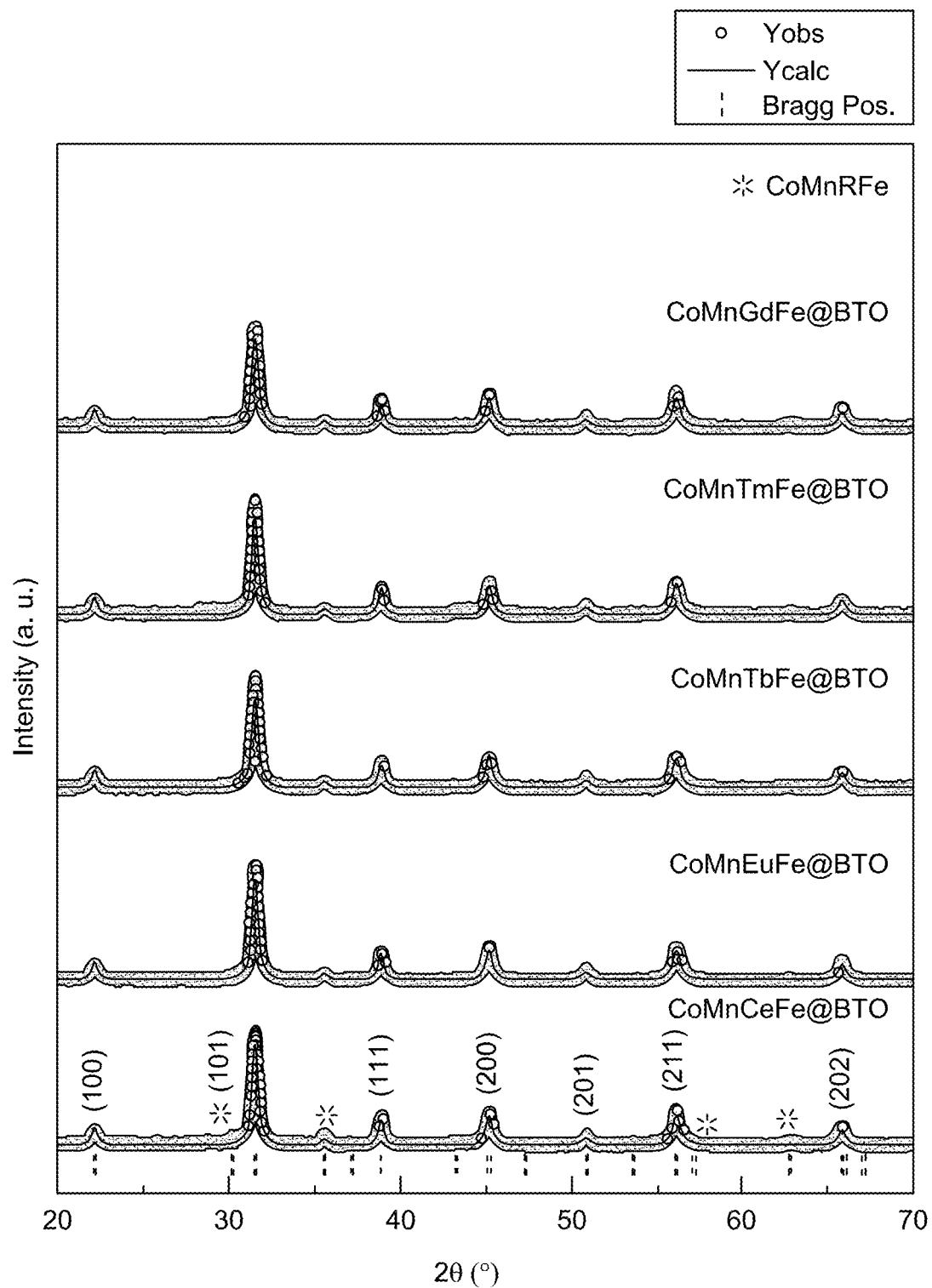
FIG. 4 illustrate X-ray crystallography (XRD) patterns of synthesized MENs, according to certain embodiments.

In some embodiments, the MEN is substantially spherical in shape and has an average size of 5-30 nm, preferably 10-25 nm, or 15-25 nm where the spheres are agglomerated to form aggregates with an average size of 50-500 nm, preferably 100-400 nm, or 200-300 nm. In some embodiments, the degree of agglomeration varies with the MEN R element, with the lighter elements in the lanthanide series (Ce, Eu) having mostly an agglomerated network, and the heavier elements (Gd, Tb, Tm) having a mixture of agglomerated networks of the spherical particles and separate large aggregates (FIG. 5). FIG. 4 depicts the XRD patterns of the MEN with the (100) peak at 21-24°, preferably 21.5-23.5°, or 22-23°, the (101) peak at 30-33°, preferably 30.5-32.5°, or 31-32°, the (111) peak at 37-40°, preferably 37.5-39.5°, or 38-39°, the (200) peak at 44-47°, preferably 44.5-46.5°, or 45-46°, the (201) peak at 50-53°, preferably 50.5-52.5°, or 51-52°, the (211) peak at 55-58°, preferably 55.5-57.5°, or 56-57°, and the (202) peak at 65-68°, preferably 65.5-67.5°, or 66-67°.

In some embodiments, MENs have an average crystallite size of 30-45 nm, preferably 32-40 nm, or 34-37 nm. The crystallite sizes of the MEN are large due to the doping of the large lanthanide element, thereby distorting and straining the crystal structure. In FIG. 7 the appearance of lattice fringes propose that the MEN are highly crystalline and the interface between SFNP core and BTO phases is clear. Therefore, there is a strong magnetoelectric coupling at the interface of the core-shell nanocomposite, due to the strain transfer that occurs at the interface between magnetic core and ferroelectric shell. The magnetoelectric coupling effect is strongly dependent on the magnetostriction effect imparted by the magnetic core. Therefore, the highly magnetostrictive core, due to the increased strain caused by the lanthanide doping, combined with high electrical resistivity shell, improves magnetoelectric properties. The strain imposed on the core, transfers to the shell with the application of magnetic field, which leads to the production of an electric field in the ferroelectric BTO. In some embodiments, MENs have a magnetoelectric coefficient of 12-25 millivolt per centimeter oersted (mV/cm Oe), preferably 14-22, or 16-20 mV/nm Oe at 1800 Oe. In some embodiments, MENs have a zeta potential of −17 to 13 mV, preferably −17 to −15 or 10-13 mV.

An effective amount of MENs is used for treating a colorectal cancer, where the MEN are selective for HCT-116 cells. In some embodiments, composition of MEN has a concentration of 1300-1500 μg/mL, preferably 1300-1400, or 1300-1350 μg/mL to inhibit a growth of HCT-116 cells by at least 10%, preferably 20%, 30%, or all HCT-116 cells. In some embodiments, the MEN are non-toxic to HEK-293 cells at a concentration of 1300-1500 μg/mL, preferably 1400-1500, or 1450-1500 μg/mL. Some embodiments include administering to the subject the MEN in an amount effective to decrease the average cancer cell viability of the cancer by more than 10%, preferably 20%, 30% or decrease all cancer cell viability. In a preferred embodiment, the subject is a human. In some embodiments, the subject may be an animal. In some embodiments, the colorectal cancer treatment includes an anti-cancer drug, where the anti-cancer drug is associated to the MENs. In some embodiments the association may be through an ionic bond and/or covalent bond. In an embodiment, the anti-cancer drug associated to the MENs is administered to a patient and a magnetic field is applied to the exterior of the patient to navigate the drug to a desired part of the patient body. In an embodiment the anti-cancer drug is any pharmaceutical compound for treating colorectal cancer known in the art.

Referring to FIG. 1, a schematic flow diagram of the method 100 of forming the rare earth metal doped SFNP core is illustrated. The method 100 is described with reference to formation of the shell material illustrated in FIG. 2 and the formation of MEN illustrated in FIG. 3. The order in which the method 100 is described is not intended to be construed as a limitation, and any number of the described method steps may be combined in any order to implement the method 100. Additionally, individual steps may be removed or skipped from the method 100 without departing from the spirit and scope of the present disclosure.

At step 102, the method 100 includes forming a mixture of at least one iron (III) salt, at least one cobalt (II) salt, and at least one manganese (II) salt in water. The mixture is of a formula of $Co_xMn_{1-x}R_{2-y}Fe_yO_z$ wherein x=0.1-0.9, y=1.90-1.99, and z=3-5. In an embodiment, the formula for the mixture is $Co_{0.8}Mn_{0.2}R_{0.02}Fe_{1.98}O_4$. In an embodiment, the iron (III) salt is at least one selected from the group consisting of iron (III) nitrate, iron (III) chloride, iron (III) sulfate, iron (III) carbonate, and hydrates thereof. In an embodiment, the cobalt (II) salt is at least one selected from the group consisting of cobalt (II) nitrate, cobalt (II) chloride, cobalt (II) carbonate, cobalt (II) sulfate, and hydrates thereof. In an embodiment, the manganese (II) salt is at least one selected from the group consisting of manganese (II) nitrate, manganese (II) chloride, manganese (II) carbonate, manganese (II) sulfate, and hydrates thereof. In an embodiment, the iron (III) salt is iron (III) nitrate nonahydrate [$Fe(NO_3)_3 \cdot 9H_2O$], the cobalt (II) salt is cobalt nitrate hexahydrate [$Co(NO_3)_2 \cdot 6H_2O$], the manganese (II) salt is manganese (II) nitrate tetrahydrate [$Mn(NO_3)_3 \cdot 4H_2O$].

At step 104, the method 100 includes dissolving at least one rare earth metal salt from the group consisting of Ce, Eu, Gd, Tb and Tm in acid at a temperature greater than 150 degrees centigrade (° C.), preferably 150-200, or 170-190° C. to for at least 1 hour, preferably 1-4 hours, or 2-3 hours, to form a dissolved rare earth metal solution. In some embodiments, the rare earth metal salt is a sulfate, nitrate, chloride, or oxide of Ce, Eu, Gd, Tb and Tm. In some embodiments, the rare earth metal salt is one or more selected from a group of ($Ce(NO_3)_2 \cdot 6H_2O$) cerium nitrate, ($EuN_3O_9 \cdot 5H_2O$) europium nitrate, $Tb_4O_7$ terbium oxide, $Tm_2O_3$ thulium oxide, and $Gd_2O_3$ gadolinium oxide. In an embodiment, the acid is selected from the group consisting of hydrochloric acid, hydrobromic acid, and sulfuric acid. In an alternative embodiment, the at least one rare earth metal salt may be thawed in 12 ml of conc. hydrochloric acid (HCl) at 180° C. under constant stirring to form the dissolved rare earth metal solution.

At step 106, the method 100 includes adjusting the pH of the dissolved rare earth metal solution to at least 10, preferably 10-12, or 10.5-11.5, with a base to form an adjusted dissolved rare earth metal solution. In some embodiments, the base can be an organic base or an inorganic base that is conventionally known in the art. In an embodiment, 2 Molar (M) sodium hydroxide (NaOH) was added dropwise under constant stirring so as to attain the pH of dissolved rare earth metal solution to about 11.

At step 108, the method 100 includes combining the mixture and the adjusted dissolved rare earth metal solution to form a synthetic solution.

At step 110, the method 100 includes subjecting the synthetic solution to ultrasonic irradiation with a power of at least 50 W, preferably 50-100, or 60-80 W, and a frequency of at least 10 KHz, preferably 10-30, or 15-25 kHz, for at least 1 hour, preferably 1-3 hours, or 1.5-2 hours to form a precipitate. In an alternative embodiment, the solution was exposed to the ultrasonic irradiation (Ultrasonic homogenizer UZ SONOPULS HD 2070 at a power of 70 W and a frequency of 20 KHz for 1 h to form the precipitate.

At step 112, the method 100 includes washing the precipitate with water and drying at a temperature greater than 150° C., preferably 150-200, or 170-190° C. for at least 8 hours, preferably 8-20 hours, or 10-15 hours to get a dried material. In an alternative embodiment, the product was washed several times with hot de-ionized (DI) water then dried at 180° C. for 12 h to obtain the dried material.

At step 114, the method 100 includes pulverizing the dried material to get the rare earth metal doped SFNP core material. In an alternative embodiment, the material might be crushed by an agate mortar to get the rare earth metal doped SFNP core material.

Figure 2:
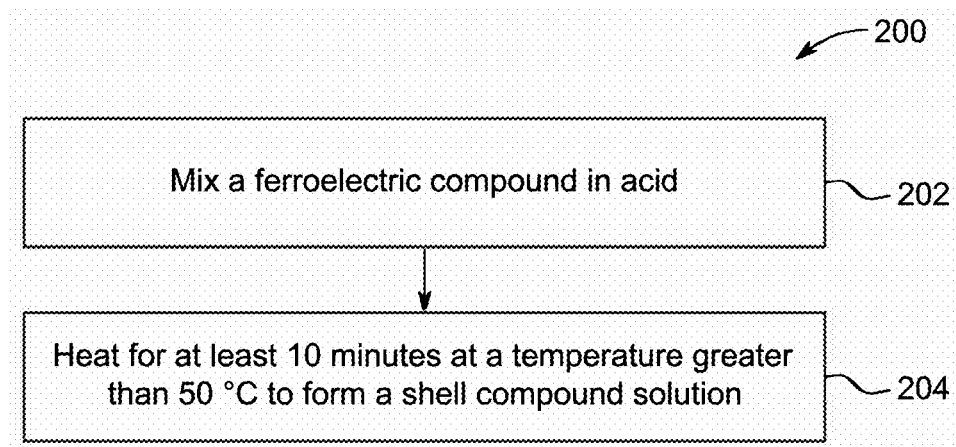
FIG. 2 is a schematic flow diagram of a method of forming a shell material, according to certain embodiments.

Referring to FIG. 2, a schematic flow diagram of the method 200 of forming a shell material solution is illustrated. The order in which the method 200 is described is not intended to be construed as a limitation, and any number of the described method steps may be combined in any order to implement the method 200. Additionally, individual steps may be removed or skipped from the method 200 without departing from the spirit and scope of the present disclosure.

At step 202, the method 200 includes mixing a ferroelectric compound in acid and heating for at least 10 minutes, preferably 10-60, or 30-40 mins at a temperature greater than 50° C. to form a shell compound solution. In an embodiment, a proper stoichiometric amount of titanium (IV) isopropoxide was dissolved in 50 milliliter (ml) ethanol and 50 ml de-ionized (DI) water with continuous stirring for half an hour at 80° C. temperature. In another embodiment, the barium citrate solution was prepared by dissolving an appropriate amount of barium carbonate ($BaCO_3$) in 10 ml ethanol and 10 ml DI water under constant stirring for half an hour at room temperature.

At step 204, the method 200 includes heating for at least 10 minutes at a temperature greater than 50° C., preferably 50-100, or 70-90° C. to form the shell compound solution. In an alternative embodiment, solutions were thoroughly mixed in a single beaker with 4.2 grams (g) of citric acid and kept stirring for 30 min and heating at 80° C.

Figure 3:
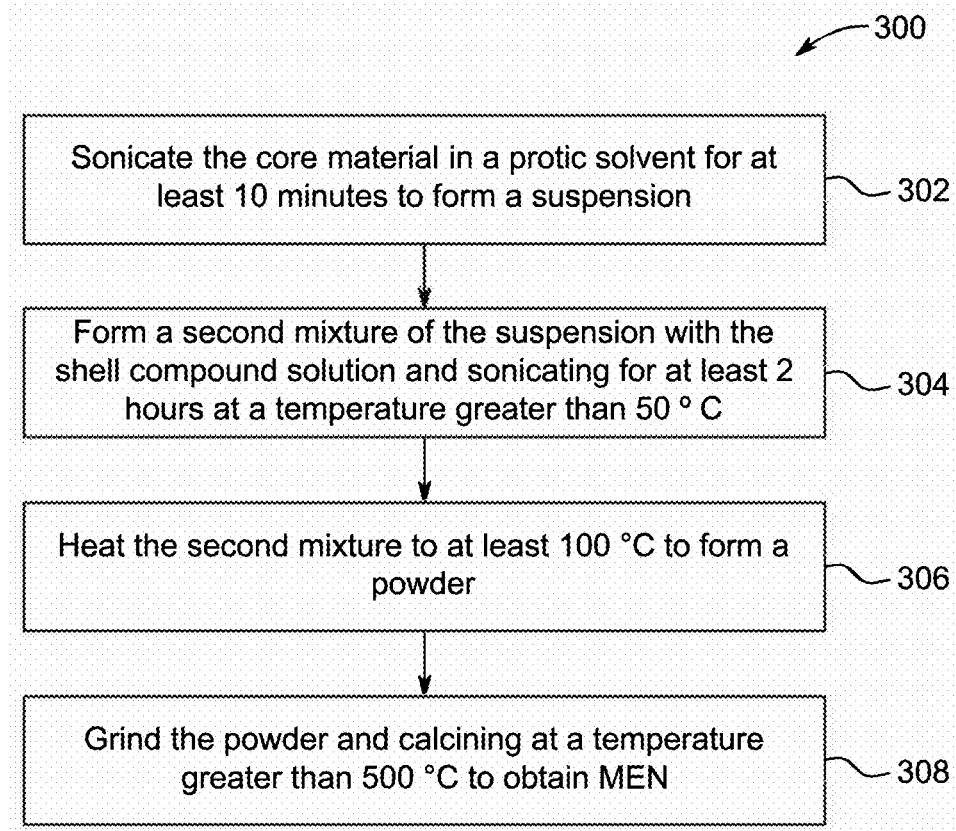
FIG. 3 is a schematic flow diagram of a method of forming MENs, according to certain embodiments.

Referring to FIG. 3, a schematic flow diagram of the method 300 of forming the MEN is illustrated. The order in which the method 300 is described is not intended to be construed as a limitation, and any number of the described method steps may be combined in any order to implement the method 300. Additionally, individual steps may be removed or skipped from the method 300 without departing from the spirit and scope of the present disclosure.

At step 302, the method 300 includes sonicating the core material in a protic solvent for at least 10 minutes, preferably 10-60, or 30-40 minutes to form a suspension. In an alternative embodiment, an appropriate amount of the prepared spinel ferrite was properly dispersed in ethanol by sonicating for 30 min.

At step 304, the method 300 includes forming a second mixture of the suspension with the shell compound solution and sonicating for at least 2 hours, preferably 2-4 hours, or 2.5-3 hours at a temperature greater than 50° C., preferably 50-100, or 70-90° C. In an alternative embodiment, the suspension was thoroughly mixed with a BTO precursor solution followed by vigorously sonicating at 80° C. for 2 h.

At step 306, the method 300 includes heating the second mixture to at least 100° C., preferably 100-150, or 120-130° C. to form a powder. In an alternative embodiment, the resultant mixture was heated to 80° C. without stirring until it became near to gel and then the temperature raised to 120° C. until the gel was formed and burned.

At step 306, the method 300 includes grinding the powder and calcining at a temperature greater than 500° C., preferably 500-1000, or 750-850° C. to obtain MEN. In an alternative embodiment, the obtained powder was grounded in an agate mortar then calcined at 800° C. for 5 h to obtain a core-shell nanocomposite powder.

EXAMPLES

The following examples describe and demonstrate exemplary embodiments of the magnetoelectric nanoparticles (MENs) described herein for treating colorectal cancer. The examples are provided solely for the purpose of illustration and are not to be construed as limitations of the present disclosure, as many variations thereof are possible without departing from the spirit and scope of the present disclosure.

Example 1: Preparation of the Core Material (Spinel Ferrite Nanoparticles or SFNP's)

A sonochemical approach was utilized to synthesize $Co_{0.8}Mn_{0.2}R_{0.02}Fe_{1.98}O_4$ (R=cerium (Ce), europium (Eu), gadolinium (Gd), terbium (Tb), and thulium (TM). The following reagents iron (III) nitrate nonahydrate [$(Fe(NO_3)_3 \cdot 9H_2O$], cobalt nitrate hexahydrate [$Co(NO_3)_2 \cdot 6H_2O$], manganese (II) nitrate tetrahydrate [$Mn(NO_3)_3 \cdot 4H_2O$], $(Ce(NO_3)_3 \cdot 6H_2O)$ cerium nitrate, $(EuN_3O_9 \cdot 5H_2O)$ europium nitrate, $Tb_4O_7$ terbium oxide, $Tm_2O_3$ thulium oxide, and $Gd_2O_3$ gadolinium oxide were used as the starting materials. The specific amounts of metal nitrates were dissolved in de-ionized (DI) water while the metal oxides thawed in 12 milliliters (ml) of conc. hydrochloric acid (HCl) at 180 degrees centigrade (° C.) under constant stirring to get a homogenous solution. Further, 2M sodium hydroxide (NaOH) was added dropwise under constant stirring to attain the pH of mixed metal solution equal to 11. Further, the solution was exposed to the ultrasonic irradiation (Ultrasonic homogenizer UZ SONOPULS HD 2070 with a power of 70 W and a frequency of 20 KHz) for 1 hour (h). The product was washed several times with hot DI water then dried at 180° C. for 12 h. Finally, the material was crushed by an agate mortar to get SFNPs.

Example 2: Synthesis of Barium Titanate (BTO) Precursor Solution

A BTO precursor solution was prepared via sol-gel method. For this purpose, a stoichiometric amount of titanium (IV) isopropoxide was dissolved in 50 ml ethanol and 50 ml DI water with continuous stirring for half an hour at 80° C. temperature. In parallel, the barium citrate solution was prepared by dissolving an appropriate amount of barium carbonate ($BaCO_3$) in 10 ml ethanol and 10 ml DI water under constant stirring for half an hour at room temperature. Further, the two prepared solutions, i.e., the barium carbonate solution and the titanium (IV) isopropoxide solution, were thoroughly mixed in a single beaker with 4.2 grams (g) of citric acid under constant stirring for 30 minutes (min) and heating at 80° C.

Example 3: Synthesis of Core-Shell MENs

An appropriate amount of the prepared SFNP was properly dispersed in ethanol by sonication bath for 30 min. The suspension was thoroughly mixed with the BTO precursor solution followed by sonication at 80° C. for 2 h. The resultant mixture was heated to 80° C. without stirring until it became near to gel, and then the temperature raised to 120° C. until the gel was formed and burned, resulting in a powder. The obtained powder was grounded in an agate mortar then calcined at 800° C. for 5 h to obtain the core-shell MEN powder.

Example 4: Cell Viability by 3-(4,5-Dimethylthiazol-2-Yl)-2,5-Diphenyl Tetrazolium Bromide (MTT) Assay Both cell lines, i.e., colorectal cancer cells HCT-116, and normal HEK-293 cells were used to examine the influence of magnetic core CoMnRFe and core-shell CoMnRFe@BTO (R=Ce, Eu, Gd, Tb, and Tm) MENs. The cells were cultured in T-25 flasks containing culture media in a carbon dioxide ($CO_2$) incubator with a temperature of 37° C. The cells with 70-80% confluence were trypsinized and grown in 96-well plates. All cells were treated with various dosages of magnetic core CoMnRFe and core-shell CoMnRFe@BTO MENs (33 to 267 micrograms (µg)/0.1 milliliters (mL)) except the control group. After 48 hours of treatment, the cytotoxicity effect was observed through adding MTT solution (10 milligrams per milliliters (mg/mL)) to each well, and they were preserved for 4 hours. Further, the cells were treated with dimethyl sulfoxide (DMSO) to develop formazan crystals formation. Finally, culture plates were examined in a microplate reader (Biotek Instruments, Winooski, United States of America (USA)).

Example 5: Nuclear Morphology Examination by 4',6-Diamidino-2-Phenylindole (DAPI) Staining HCT-116 were stained with DAPI to visualize the impact of core CoMnRFe and core-shell CoMnRFe@BTO MENs on nuclear deoxyribonucleic acid (DNA) of cancer cells. HCT-116 cells were seeded in chamber slides in $CO_2$ incubator (5%) at a temperature of 37° C., allowed to attach overnight. Further, the cells were separated into two groups:

one was untreated control group and another one was treated with (88.8 μg/0.1 ml) dosage of core CoMnRFe and core-shell CoMnRFe@BTO MENs. Post of 48 h, both groups were treated with ice-cold paraformaldehyde (4%) solution then washed with phosphate-buffered saline (PBS). After that, cells were labelled with DAPI under a dark environment and kept for 30 min at room temperature. Finally, cells were washed with PBS and analyzed their morphology via a laser confocal scanning microscope (Zeiss Germany).

Example 6: Statistical Analysis

Mean±standard error (M.S.E) from control and nanoparticles (NPs) group was calculated. All statistical analyses were calculated with GraphPad Prism 9.0 (GraphPad Software). The difference between control and nanocomposites treated groups calculated by a one-way analysis of variance (ANOVA) with Dunnett's post hoc test. Error bars S.E.M. * p<0.05 versus control. In case there was no indication of significance, it was confirmed that results were non-significant.

Results and Discussion

FIG. 4 presents the powder X-ray diffraction (PXRD) patterns of all synthesized core-shell CoMnRFe@BTO (R=Ce, Eu, Gd, Tb, and Tm) MENs. It revealed the presence and the combination of two different crystallographic orientations (spinel and perovskite phases). The absence of impurities and intermediate phases confirm the successful formation of composite materials as well as the efficiency of the preparation method. The core-shell CoMnRFe@BTO MENs planes are identified as (100), (101), (111), (200), (201), (211), and (202) corresponding to the cubic structure of pure BTO while the remaining planes (220), (311), (511), and (440) correspond to CoMnRFe.

The substitution of rare earth metals with smaller ionic radii affects the structural properties as well as the magnetic and magnetostrictive properties of substituted materials. Table 1 enlists the structural parameters of CoMnRFe@BTO MENs estimated using Rietveld refinement interfaced with Full-proof software.

TABLE 1

| Sample | BTO phase | | CoMnRFe phase | | $D_{XRD}$ (nm) |
| --- | --- | --- | --- | --- | --- |
| | α (Å) | V (Å³) | α (Å) | V (Å³) | +0.05 |
| CoMnFe@BTO | 4.0177 | 64.8539 | 8.3767 | 587.777 | 27.19 |
| CoMnCeFe@BTO | 4.0146 | 64.7019 | 8.3744 | 587.308 | 32.82 |
| CoMnEuFe@BTO | 4.0098 | 64.4696 | 8.3641 | 585.129 | 41.25 |
| CoMnGdFe@BTO | 4.0136 | 64.6565 | 8.3772 | 587.901 | 35.04 |
| CoMnTbFe@BTO | 4.0132 | 64.6381 | 8.3765 | 587.744 | 33.11 |
| CoMnTmFe@BTO | 4.0137 | 64.6599 | 8.3736 | 587.142 | 38.3 |

It can be clearly observed from the Table 1 that the lattice parameters fluctuate with changing the type of the dopant in CoMnRFe (R=Ce, Eu, Tb, Tm, or Gd) due to the differences in ionic radii of different doping elements. There are two main prominent effects observed when the rare earth large ions are substituted with pristine ions are lattice constant and crystallite size. The rare earth ions from the lanthanide series possess different sizes and usually occupy B-site (octahedral). Therefore, the ionic radii difference between the rare earth ion and host ferrite ion $r_{Fe}^{3+}$ (0.67 angstrom (Å)) may result in microstrain causing distortions in octahedral and tetrahedral sites of lattice (deformation of spinel structure). Consequently, an increase in the lattice constant 'a' of CoMnRFe is expected due to the substitutions of rare earth atoms (CoMnRFe; R=Ce, Eu, Tb, Tm, or Gd), which exhibit larger size with the host smaller size Fe atoms $r_{Fe}^{3+}$ (0.67 Å). Nevertheless, it is noticeable from the Table 1 that the lattice parameter 'a' is decreased with doping the rare earth in the ferrite structure. Introducing large, rare-earth ions into the CoMnRFe causes the distortion in octahedral and tetrahedral symmetry and deformation of spinel crystal. Hence, results were justified either by the deposition in the grain boundary which resists the growth of cell parameters or the creation of Fe vacancies that might decrease the lattice parameters. The crystallite size estimated using Debye-Scherrer equation occurred in the range of 27 to 41 nm.

Figure 5A:
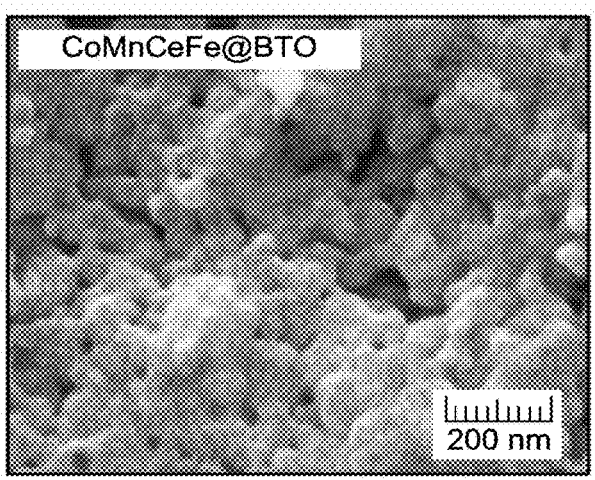
FIG. 5A-5E illustrates scanning electron microscope (SEM) images of CoMnRFe@BTO (R=cerium (Ce) (FIG. 5A), europium (Eu) (FIG. 5B), gadolinium (Gd) (FIG. 5C), terbium (Tb) (FIG. 5D), and thulium (Tm) (FIG. 5E)) MENs, according to certain embodiments.
Figure 5B:
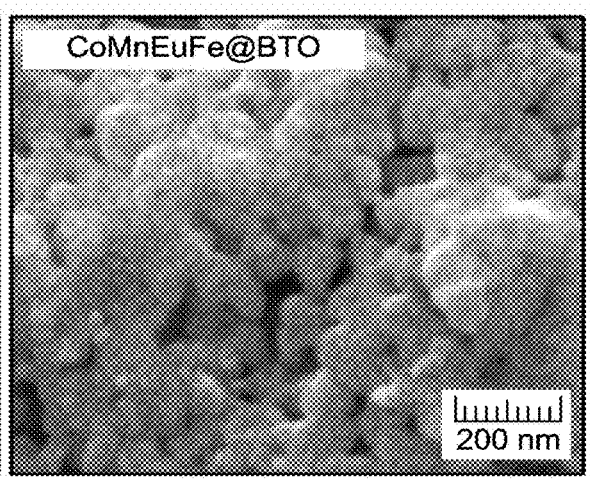
Figure 5C:
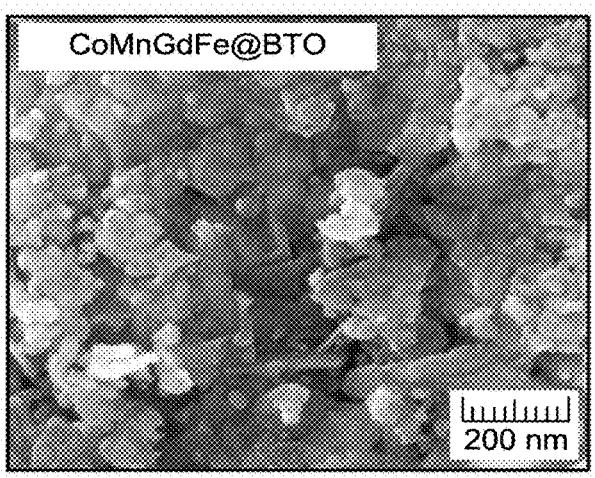
Figure 5D:
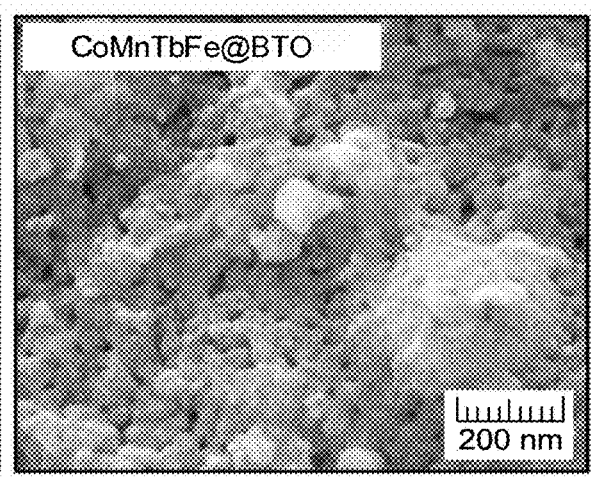
Figure 5E:
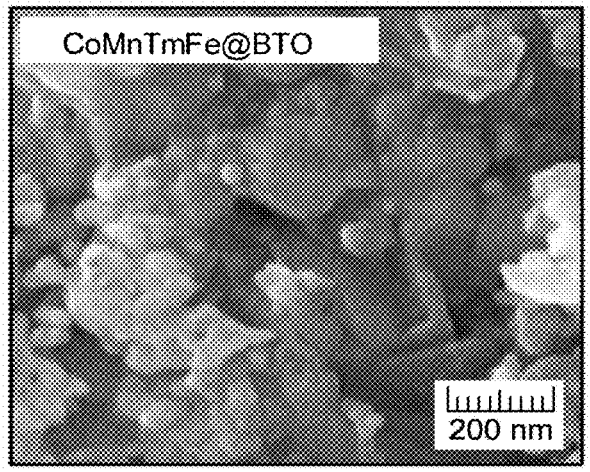
Figure 6A:
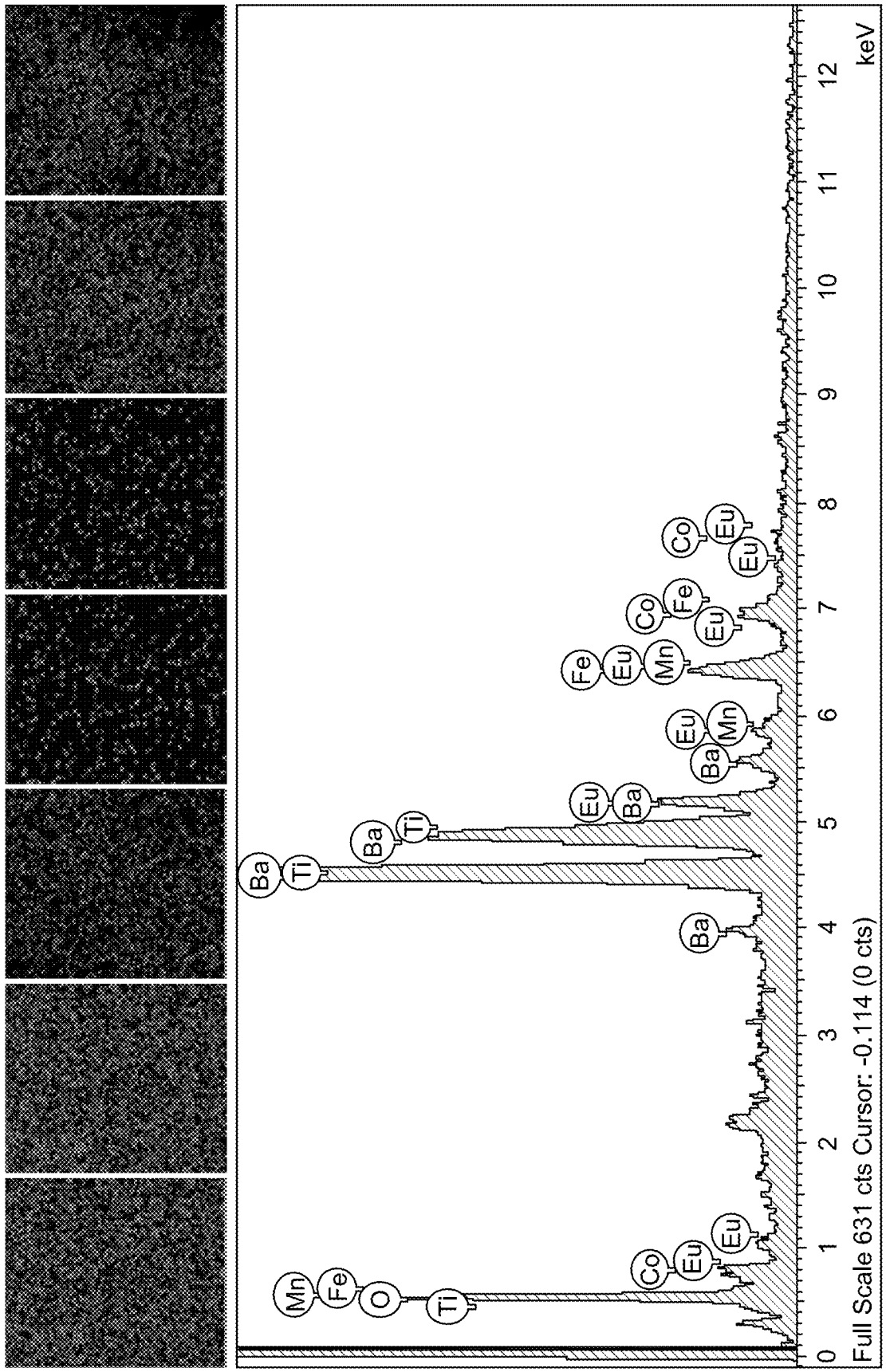
FIGS. 6A-6B illustrate energy-dispersive X-ray (EDX) spectra and elemental maps of CoMnEuFe@BTO (FIG. 6A), and CoMnTbFe@BTO MENs (FIG. 6B), according to certain embodiments.
Figure 6B:
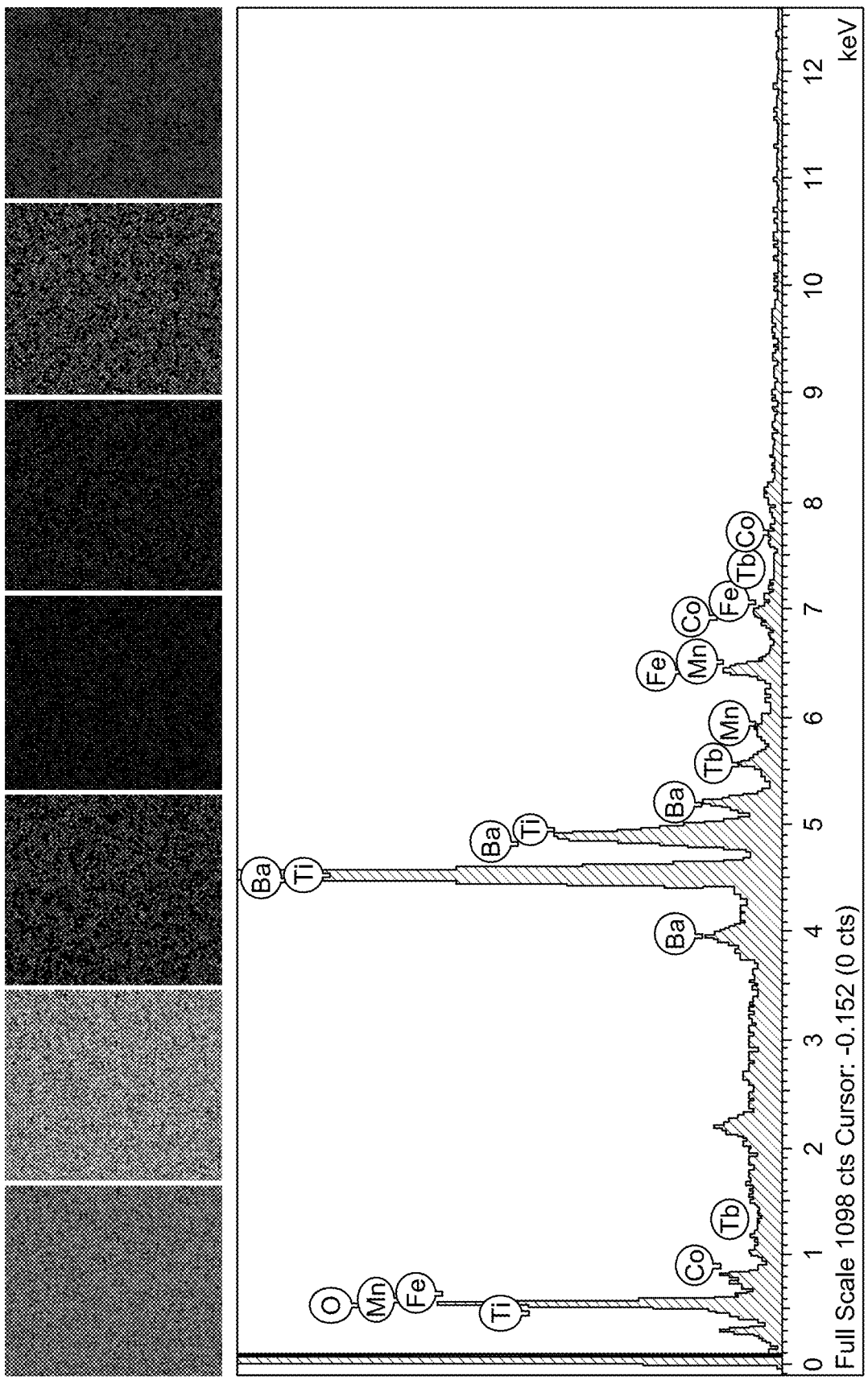

FIGS. 5A-5B show the SEM micrographs of the as-prepared CoMnRFe@BTO (R=Ce, Eu, Gd, Tb, and Tm) MENs. The composites exhibit diphase (bright and medium dark regions). Overall surface morphologies show nearly dense and aggregated spherical grains. The differences in the morphology shown in FIGS. 5A-5E with changing the core type are due to shape, degree of agglomeration, and different behavior of host spinel ferrite CoMnRFe (R=Ce, Eu, Gd, Tb, and Tm) in each composition, respectively. The EDX spectra and elemental color maps of CoMnRFe@BTO (R=Eu and Tb) are illustrated in FIGS. 6A-6B. The spectra of core-shell emphasized the existence of Ba, Ti, Co, Mn, Fe, O as well as rare-earth elements in CoMnRFe@BTO (R=Eu and Tb) respectively. No trace of any impurity was found indicating purity of the samples.

Figure 7A:
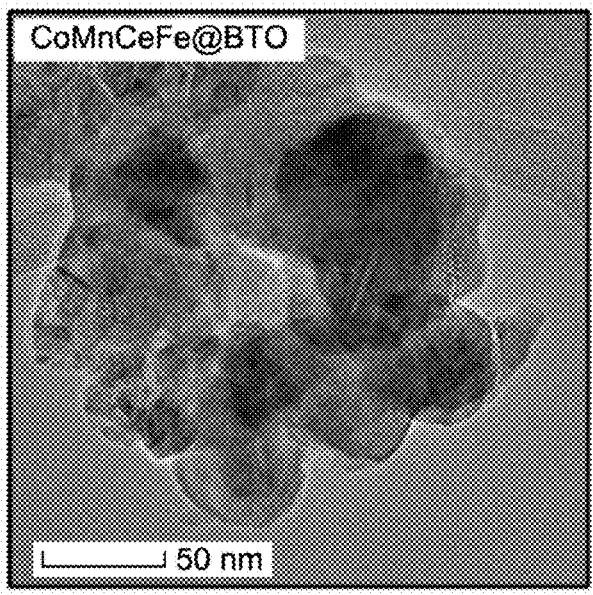
FIGS. 7A-7D illustrate transmission electron microscopy (TEM) and high-resolution transmission electron microscopy (HR-TEM) images of CoMnCeFe@BTO (FIGS. 7A-7B), and CoMnTbFe@BTO (FIGS. 7C-7D), respectively, MENs, according to certain embodiments.
Figure 7B:
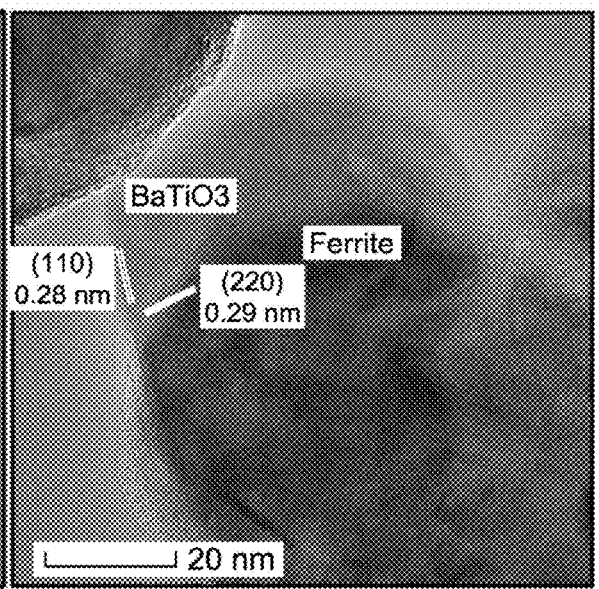
Figure 7C:
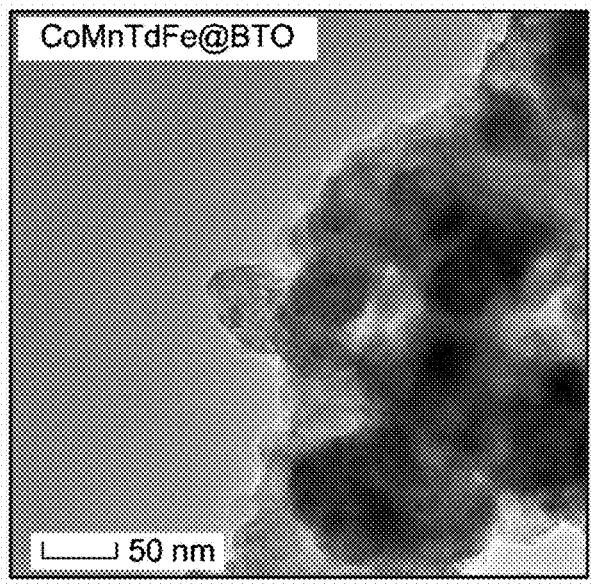
Figure 7D:
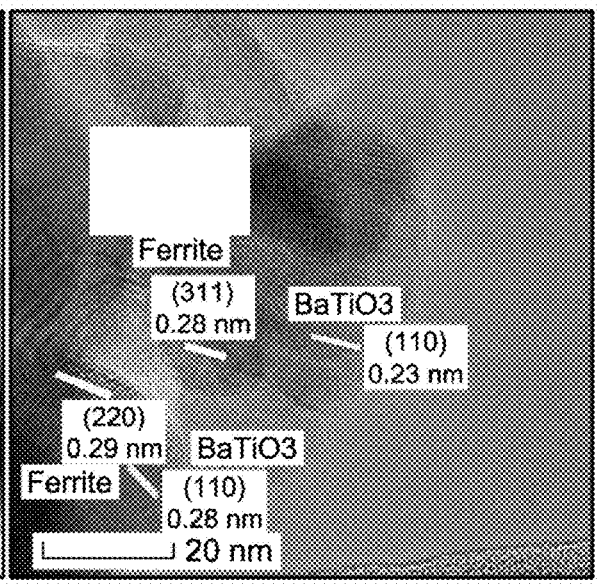

FIGS. 7A-7B depict the TEM images of the synthesized CoMnRFe@BTO (R=Ce and Tb), respectively. The two crystallite phases of the fine-grained and dense microstructure core-shell magnetoelectric nanocomposites of the BTO and spinel ferrite are confirmed by the TEM images. They illustrate the agglomeration of spinel ferrite (CoMnRFe) at the BTO matrix. Clear lattice fringes indicate that the samples are defect free and highly crystalline in nature. The interface between spinel ferrite and the BTO phases is clearly shown by high-resolution transmission electron microscopy (HR-TEM). Therefore, at this interface the movement of strain between the ferrite and ferroelectric phase might happen, and it might be suitable to build a strong ME coupling in the core-shell MEN.

Figure 8A:
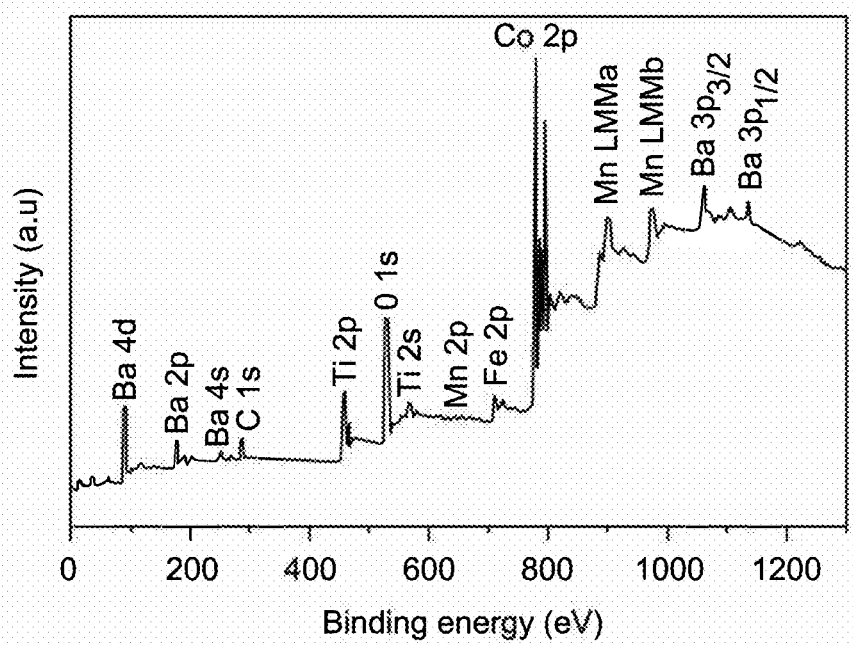
FIGS. 8A-8J illustrate X-ray photoelectron spectroscopy (XPS) spectra of CoMnFeTmBTO, and CoMnFeGdBTO MENs, according to certain embodiments.
Figure 8B:
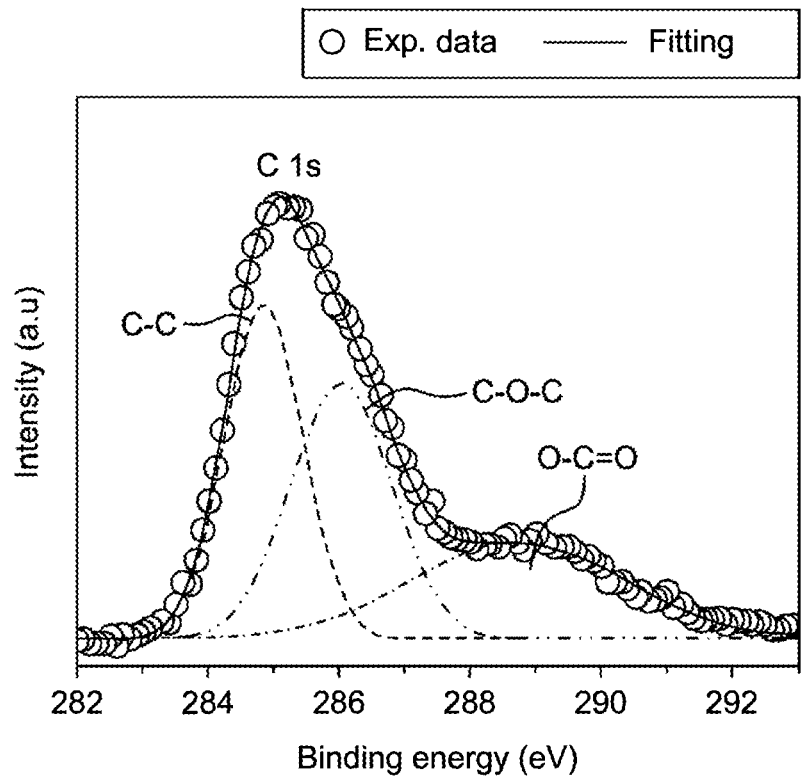
Figure 8C:
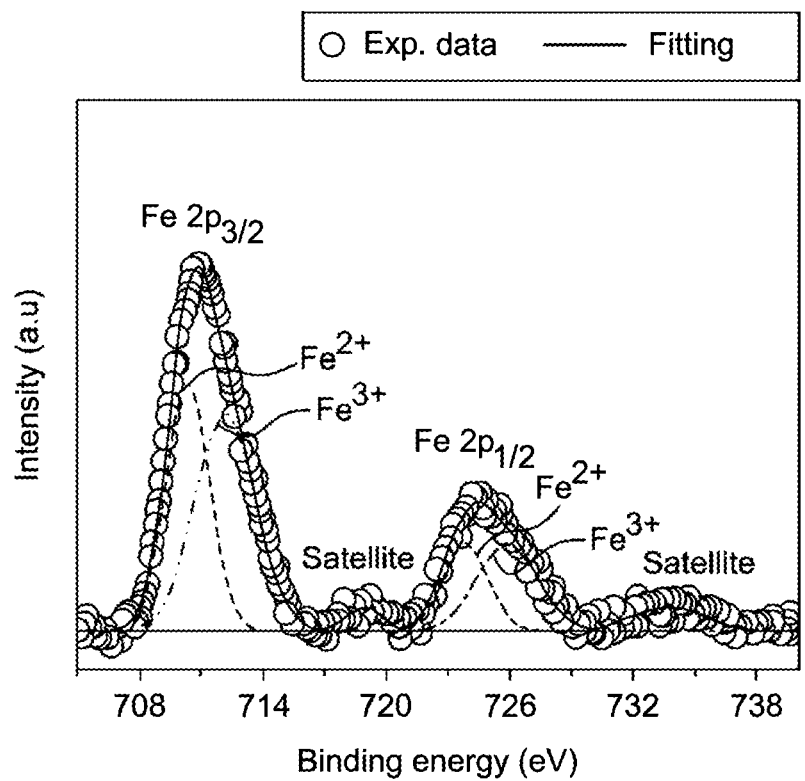

XPS analysis of the synthesized sample CoMnRFe@BTO MENs (R=Tm and Gd) was performed to study the chemical composition of each element along with the corresponding oxidation state. The analysis was started with a wide survey scan to confirm the presence of all the elements, as shown in FIG. 8A. The core-level spectra of each element of the sample were deconvoluted and presented separately in FIGS. 8B to 8J. FIG. 8B depicts the carbon (C 1s) spectrum deconvoluted into three characteristic peaks. The peak corresponding to the binding energy of 284.8 electron volt (eV) is ascribed to the C—C bonding, which is a well-known peak of adventitious carbon. The other peaks at 286.0 eV and 288.6 eV are attributed to the C—O—C and O—C=O, respectively, indicating the presence of organic contamination from the open atmosphere. FIG. 8C depicts the core level elemental peaks of Fe at a binding energy of 710.7 eV and 724.6 eV corresponding to the spin-orbit coupling of Fe 2p3/2 and Fe 2p1/2, respectively. These peaks were deconvoluted into characteristic peaks of $Fe^{2+}$ and $Fe^{3+}$ states corresponding to 710.3 eV and 712.0 eV for Fe 2p3/2 spectrum and 723.8 eV and 725.7 eV for Fe 2p1/2 spectrum, respectively. Two broad satellite peaks related to the core spectrum of Fe 2p3/2 and Fe 2p1/2 were also observed at 718.8 eV and 733.9 eV, respectively, that were well matched with literature.

Figure 8D:
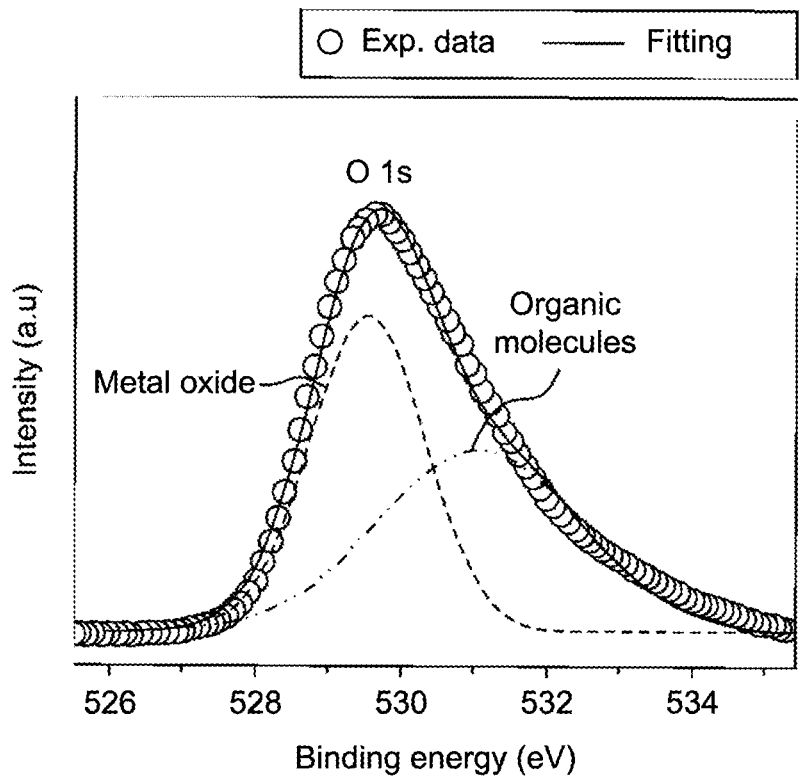
Figure 8E:
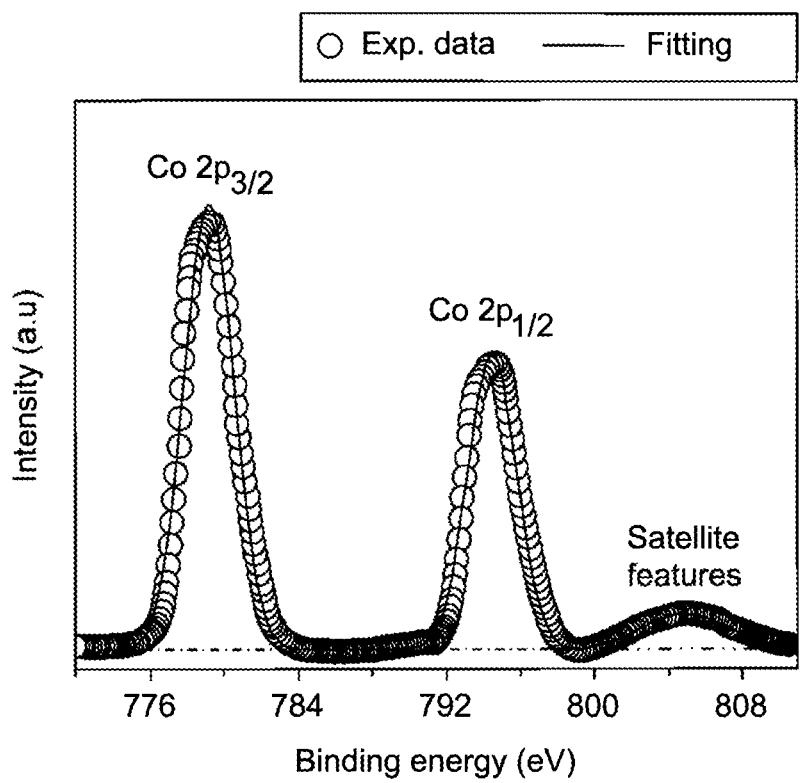
Figure 8F:
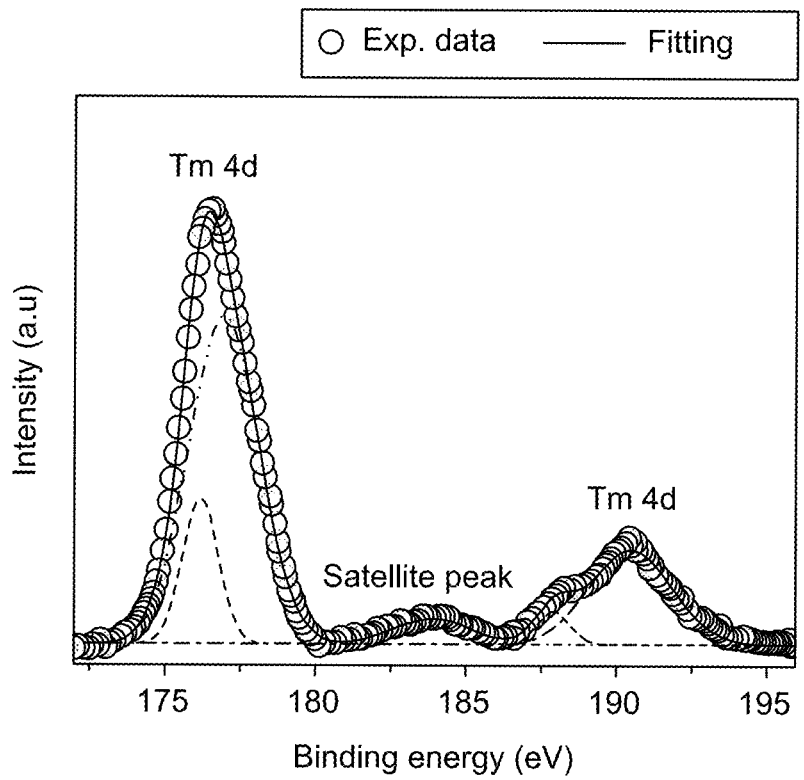
Figure 8G:
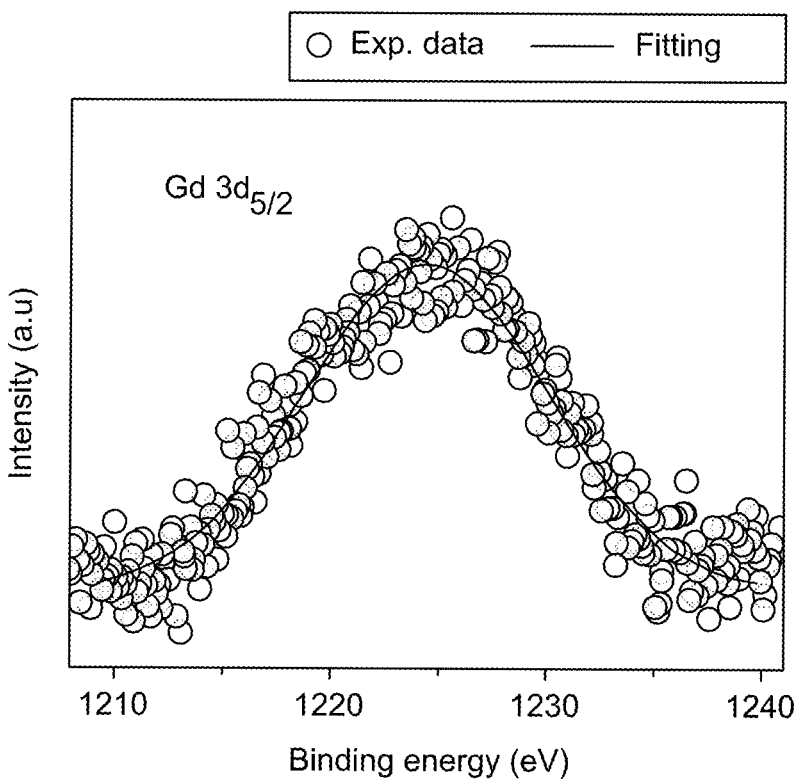

Further, the core level spectrum for O is observed at 529.7 eV was deconvoluted into two peaks as shown in FIG. 8D. The characteristic peak at 529.6 eV corresponds to the metal oxides and a relatively broad peak, which is centered around 531.0 eV, and may be assigned to the organic contaminations from the open atmosphere. The spectrum for Co displays the existence of two peaks at 778.9 eV and 794.2 eV related to Co 2p3/2 and Co 2p1/2 corresponding to $CO^{2+}$ and $Co^{3+}$ states, respectively along with a satellite peak at 804.9 eV, as shown in FIG. 8E. The presence of 778.9 and 794.2 eV peaks is due to the normal spin-orbital splitting. The atomic ratio of $Co^{2+}/Co^{3+}$ is only 0.98, verifying the dominance of $Co^{2+}$ present in the CoMnRFe. FIG. 8F illustrates the spectrum of Tm 4d5/2 and 4d3/2 with typical peaks comprised of 176.4 eV and 190.4 eV, respectively along with a satellite peak at 183.8 eV. The deconvolution of the core spectrum of Tm introduces two characteristic peaks indicating the presence of Tm in two different oxidation states with a clear dominance of $Tm^{3+}$ state corresponding to 177.3 eV. FIG. 8G demonstrates the Gd 3d5/2 spectrum with binding energy at 1224.8 eV indicating the presence of Gd with a single oxidation state as $Gd^{3+}$ state. This confirmed the effective doping of $Tm^{3+}$ and $Gd^{3+}$ ions into the Co—Mn spinel ferrite crystal.

Figure 8H:
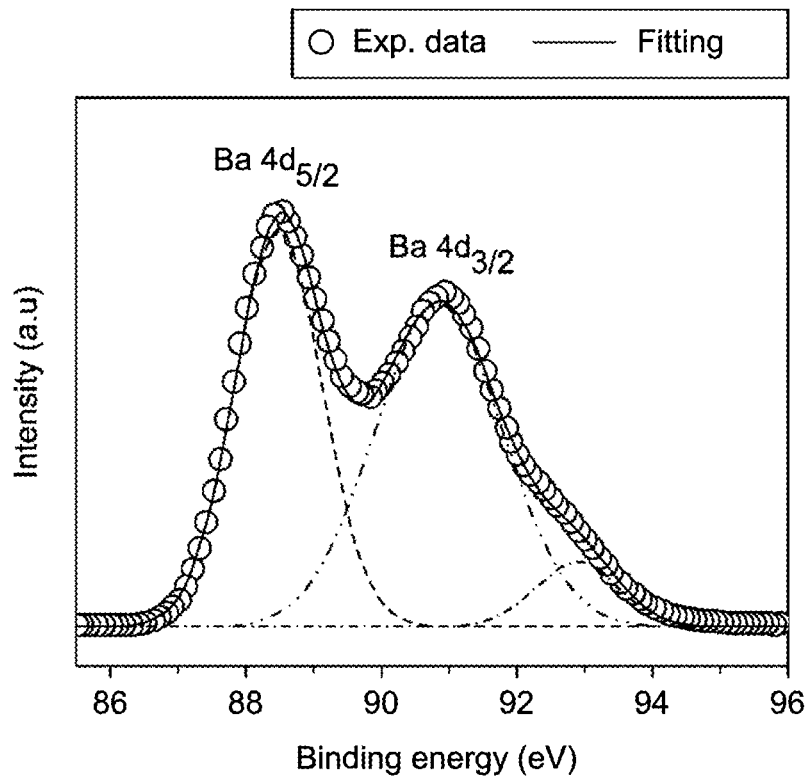
Figure 8I:
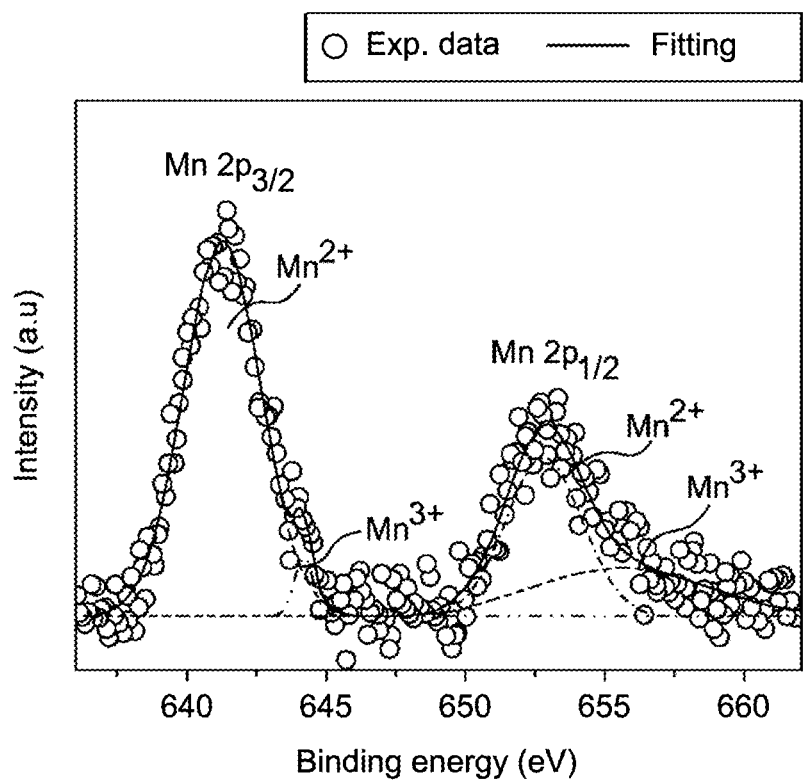
Figure 8J:
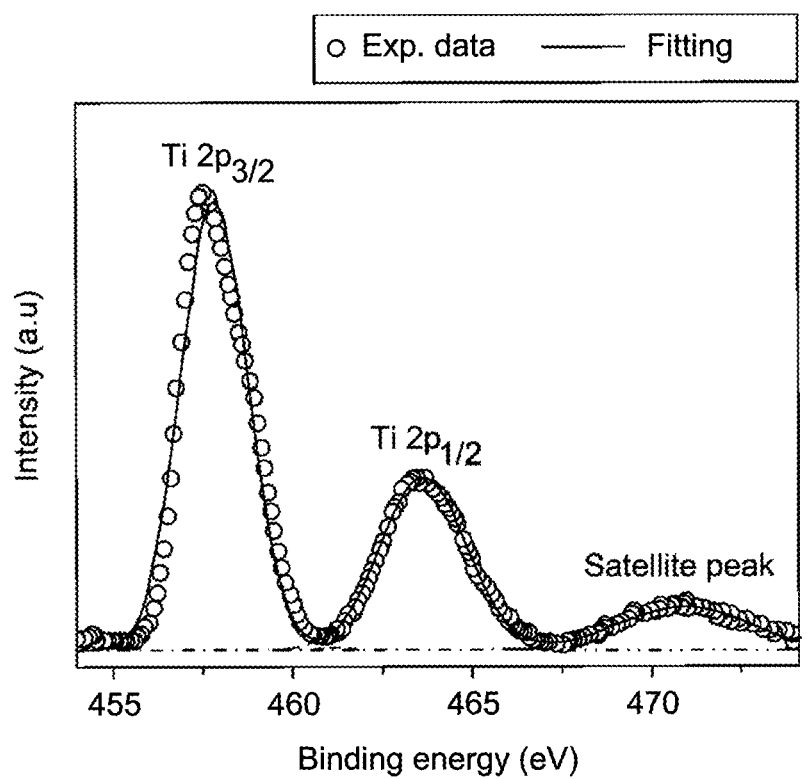

The doublet Ba peaks were composed of 4d5/2-4d3/2 spin-orbit splitting at a lower binding energy 88.5, 90.9 and satellite peak at 92.9 eV respectively may be assigned to $BaTiO_3$ and $BaCO_3$ as displayed in FIG. 8H. These peaks belong to $Ba^{2+}$ state and showed the dominance of $BaTiO_3$ over $BaCO_3$. The spectrum of Mn was observed at 641.3 eV and 652.9 eV corresponding to Mn 2p3/2 and Mn 2p1/2 respectively as shown in FIG. 8I, in agreement with the literature. The deconvolution of the Mn core spectrum presented two characteristic peaks for each Mn 2p3/2 and Mn 2p1/2 associated with $Mn^{2+}$ and $Mn^{3+}$ states. It is quite clear that $Mn^{2+}$ state has an obvious dominance over $Mn^{3+}$ state in the synthesized sample. FIG. 8J indicated that the spectrum of Ti 2p3/2 and Ti 2p1/2 spin states belong to binding energy at 457.8 and 463.5 eV corresponding to the $Ti^{3+}$ and $Ti^{4+}$ states, as a result of various titanium oxidation states and the formation of oxygen vacancies caused by the annealing procedures.

Figure 9:
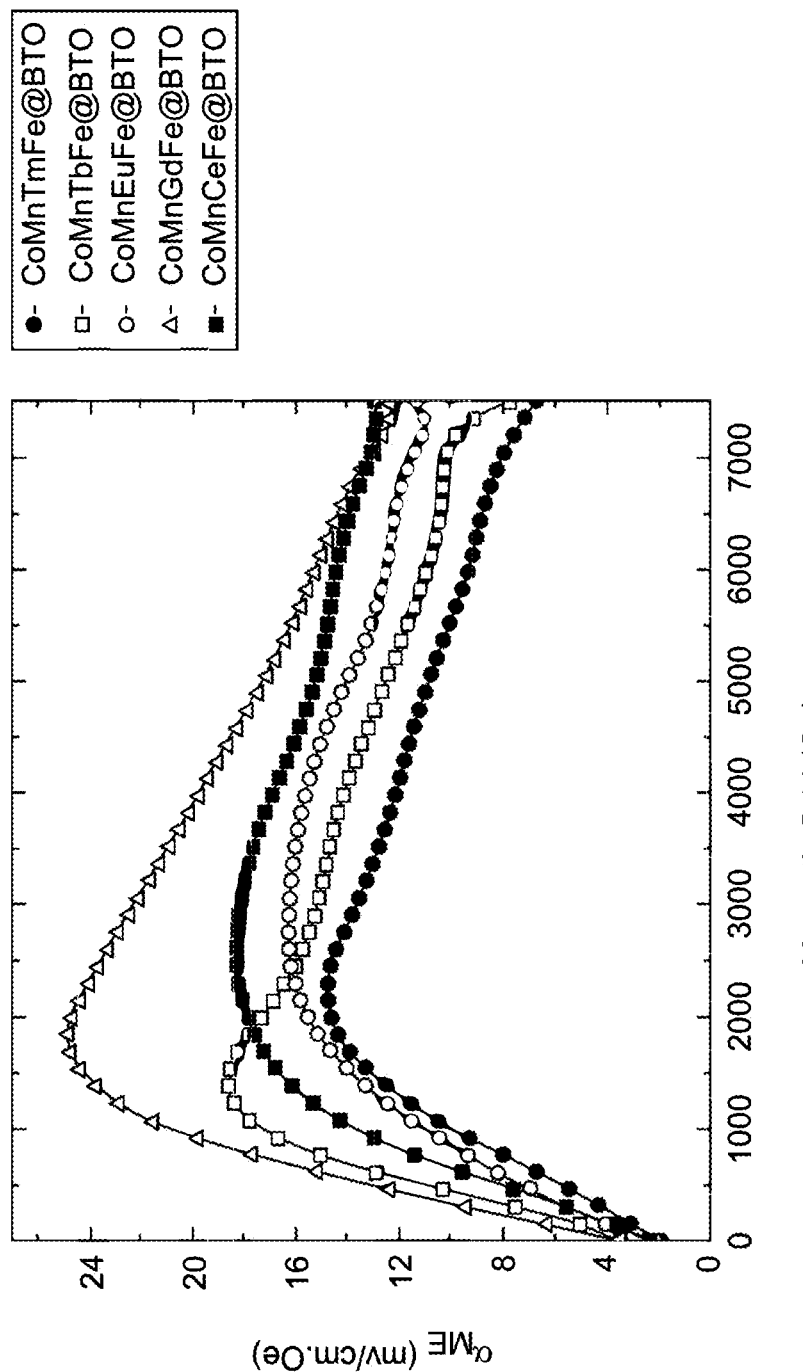
FIG. 9 illustrates variations of $\alpha_{ME}$ against magnetic field for various CoMnRFe@BTO (R=Ce, Eu, Gd, Tb, and Tm) MENs, according to certain embodiments.

FIG. 9 displays variations of an with the applied magnetic field of all the studied core-shell CoMnRFe@BTO (R=Tm, Tb, Eu, Gd, Ce) MENs. Magnetoelectric effect arises from the interfacial coupling between magnetic and ferroelectric phases. It is originated from the mechanical strain transfer that occurs at the interface between magnetic core and ferroelectric shell. The ME coupling effect is strongly dependent on the magnetostriction effect imparted by magnetic core. The highly magnetostrictive core combined with high electrical resistivity shell is an integral part of obtaining high magnetoelectric response in ME composites. The well-known hard magnetic material cobalt ferrite mixed with $Mn^{2+}$ was selected for ME analysis due to its large magnetostrictive coefficient. It was observed that the lanthanide metals exhibit the largest known magnetostrictions. Therefore, the magnetostriction measurements revealed an increment when cobalt ferrites doped with rare earth metals. The ME coupling coefficients have been determined by dynamic method to check the interaction of magnetic and electric orders at the atomic level. The measurement was conducted by superimposing the sinusoidal magnetic field ($H_{AC}$) generated by Helmholtz's coils with DC bias magnetic field ($H_{DC}$) produced by electromagnets. The linear ME coupling coefficient, $\alpha_{ME}$, for core-shell CoMnRFe@BTO (R=Ce, Eu, Tb, Tm, Gd) MENs was calculated by the following relation:

$$\alpha_{ME} = \frac{dE}{dH} = \frac{1}{t}\frac{dV}{dH} = \frac{V_{out}}{ht}$$

here t, h and $V_{out}$ are represent the sample thickness, amplitude of applied sinusoidal magnetic field, and the voltage produced across the sample surface owing to the magnetoelectric effect, respectively. FIG. 9 shows the variations of ME coupling coefficient $\alpha_{ME}$ with the applied magnetic field for core-shell CoMnRFe@BTO (R=Ce, Eu, Tb, Tm, Gd). The observed $\alpha_{ME}$ for the investigated MENs with dc magnetic fields shows an increasing behavior with respect to the increase in $H_{DC}$. $\alpha_{ME}$ inclined up to a certain maximum level followed by a decreasing trend with the increment in $H_{DC}$. Such behavior is ascribed to the magnetostrictive characteristics of ferromagnetic-CoMnRFe (R=Ce, Eu, Tb, Tm, Gd) nanocomposites. Magnetostriction of CoMnRFe (R=Ce, Eu, Tb, Tm, Gd) nanocomposites raised and reached saturation with the rise in magnetic field. Magnetic characteristics of ferromagnetic-CoMnRFe (R=Ce, Eu, Tb, Tm, Gd) compounds are directed by the magnetic domains and their size that are subjected to the strain level of ferromagnetic-CoMnRFe (R=Ce, Eu, Tb, Tm, Gd). The strain imposed on ferromagnetic-CoMnRFe (R=Ce, Eu, Tb, Tm, Gd) is expected to transfer to ferroelectric-BTO with the application of magnetic field, which lead to the production of an electric field in the ferroelectric BTO, thus, in sequence, will generate an external magnetic field dependent ME voltage in core-shell MENs. Amongst all the studied samples, the core-shell CoMnRFe@BTO MENs showed a maximum value of $\alpha_{ME}$=24.9 25 mV/cm·Oe at $H_{DC}$ $\alpha_{ME}$ 1800 Oe. Higher values of $\alpha_{ME}$ could be directly related to the magnetostriction characteristics in the core-shell MEN sample. Also, the lower value of $\alpha_{ME}$ might be correlated to the smaller resistivity and higher leakage current in the other core-shell CoMnRFe@BTO MENs (R=Tm, Tb, Eu, Ce).

The results of zeta potential measurements of CoMnRFe@BTO MENs are presented in Table 2. It has been observed that the doping of Tm in MENs increased the positive surface charge on the surface of CoMnTmFe@BTO, indicating that the surface charge behavior changed after doping with Tm. The CoMnTbFe@BTO MENs showed a positive surface charge (0.0469 mV) which reduced as compared to CoMnTmFe@BTO MENs, indicating that CoMnTbFe@BTO is less stable than CoMnTmFe@BTO MENs. Conversely, doping with Eu in MENs exhibited a negative charge on the surface of CoMnEuFeFe@BTO MENs, while doping of Gd in CoMnGdFe@BTO MENs caused a positive surface charge (0.296 mV). It was observed that doping of Ce into CoMnCeFe@BTO MENs yielded an increased surface charge to −15.6 mV indicating its high stability.

TABLE 2 represents the results of zeta potential
measurements of CoMnRFe@BTO MENs.

| Sample | Zeta potential (mV) |
|---|---|
| $Co_{0.8}Mn_{0.2}Tm_{0.02}Fe_{1.98}O_4$@BTO MENS | 11.3 |
| $Co_{0.8}Mn_{0.2}Tb_{0.02}Fe_{1.98}O_4$@BTO MENS | 0.0469 |
| $Co_{0.8}Mn_{0.2}Eu_{0.02}Fe_{1.98}O_4$@BTO MENS | −2.43 |
| $Co_{0.8}Mn_{0.2}Gd_{0.02}Fe_{1.98}O_4$@BTO MENS | 0.296 |
| $Co_{0.8}Mn_{0.2}Ce_{0.02}Fe_{1.98}O_4$@BTO MENS | −15.6 |

Figure 10A:
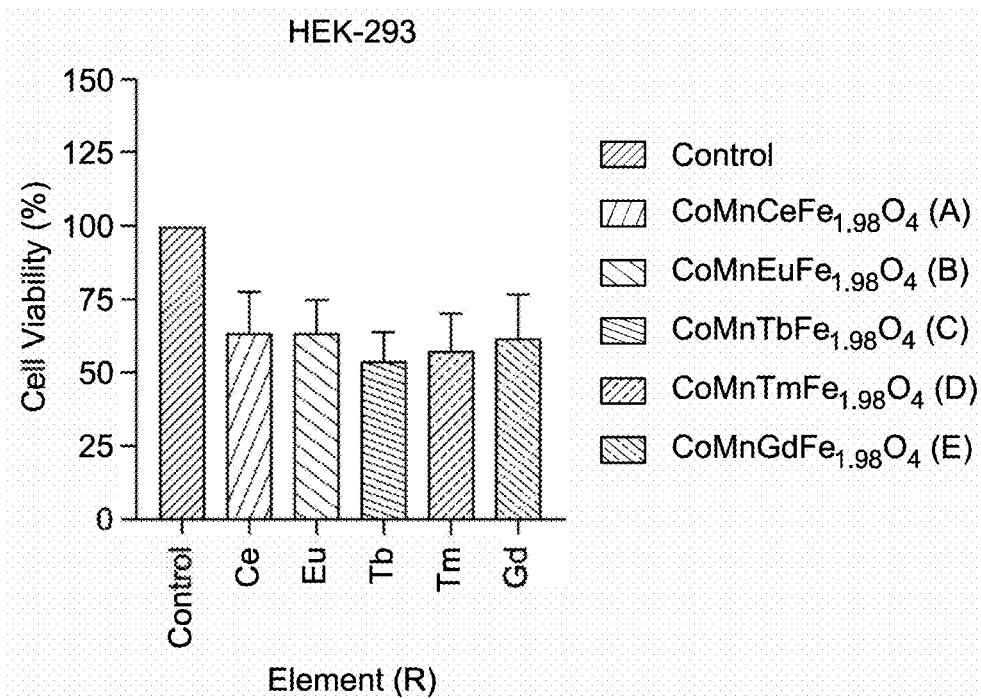
FIGS. 10A-10B show a cell viability of a human embryonic kidney (HEK-293) cell line, and a human colorectal cancer HCT-116 cell lines, respectively, using 3-(4,5-dimethylthiazol-2-yl)-2,5-diphenyl tetrazolium bromide (MTT) assay, on treatment with the various CoMnRFe NPs (R=Ce, Eu, Gd, Tb, and Tm) MENs, according to certain embodiments.
Figure 10B:
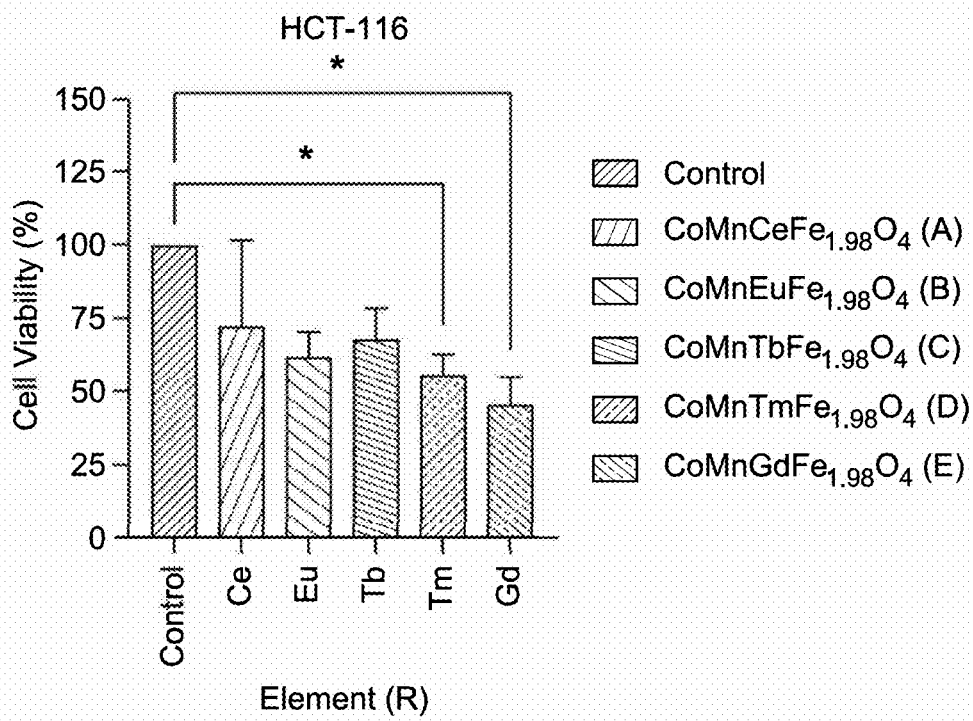

The cell viability assessment studies showed the cytotoxic effect of magnetic core CoMnRFe (R=Ce, Eu, Gd, Tb, Tm) and core-shell CoMnRFe@BTO (R=Ce, Eu, Gd, Tb, Tm) MENs on normal (HEK-293) and cancerous (HCT-116) cell lines. After 48 h of treatment, it was found that the magnetic core CoMnRFe showed a selective significant inhibitory effect p<0.05 on colon cancer (HCT-116) cells at the concentration of (141.75 μg/0.1 ml) as depicted in FIG. 10B. However, a non-significant inhibition on the normal and non-cancerous cells (HEK-293) was observed after the treatment with the same core CoMnRFe (FIG. 10A) where the percentage of cell viability was higher than HCT-116 cells.

Figure 11A:
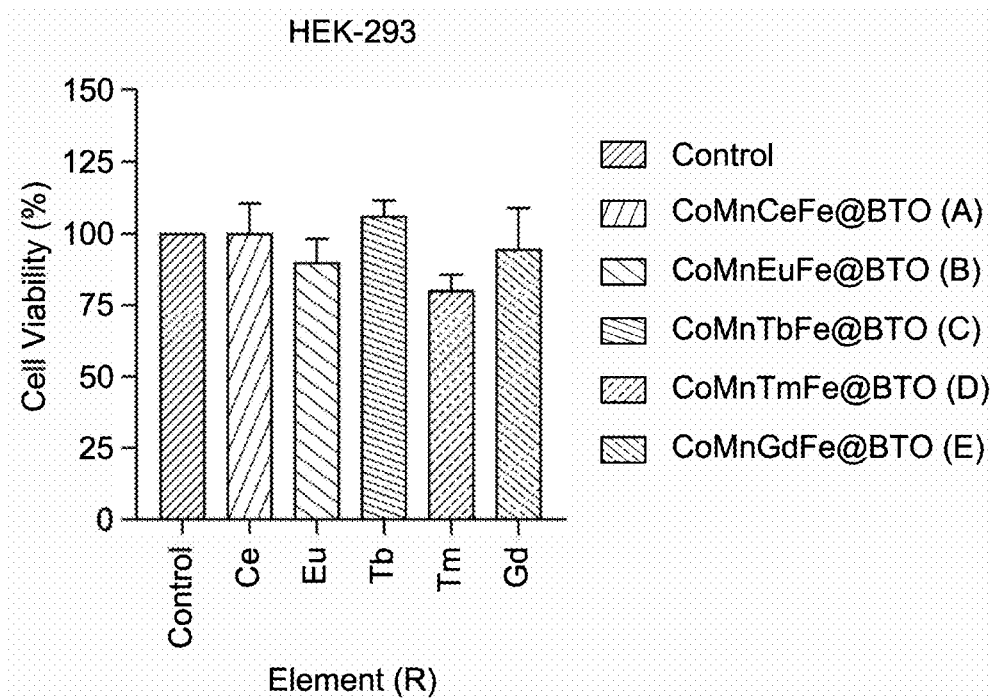
FIGS. 11A-11B illustrate the cell viability of the HEK-293 cell lines, and the human colorectal cancer HCT-116 cell lines, respectively, using MTT assay, with CoMnRFe@BTO MENs, according to certain embodiments.
Figure 11B:
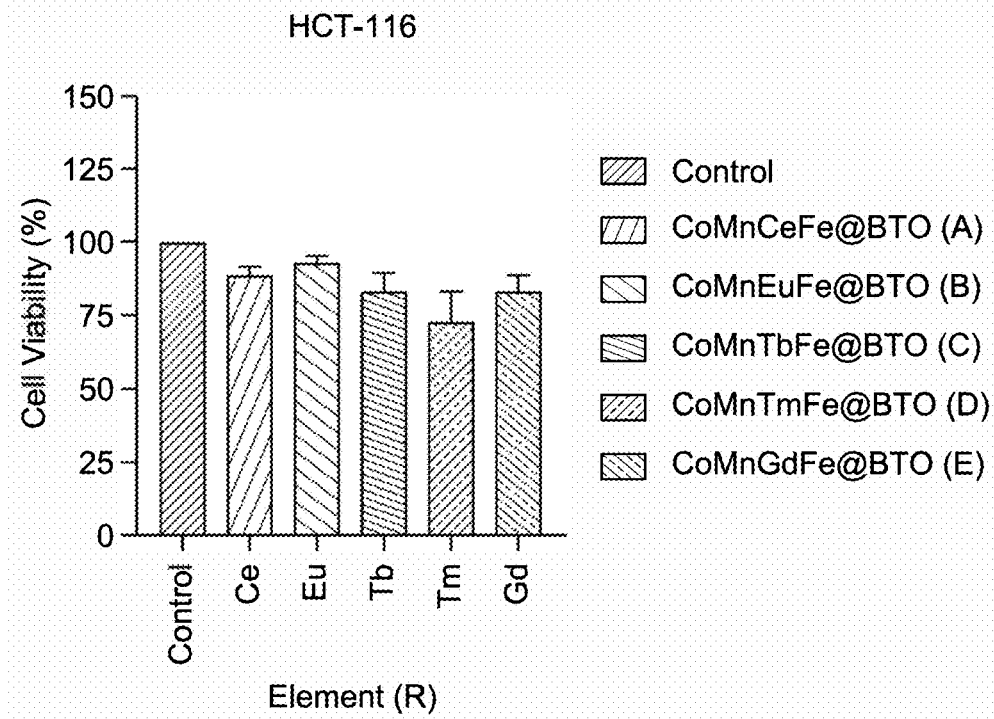

Similarly, both cell lines were treated with CoMnRFe@BTO (R=Ce, Eu, Tb, Tm, and Gd) MENs, and the results revealed that cell proliferation was more favorable in case of the BTO coating core-shell MENs than with uncoated ones. The BTO exhibited recovery effect on HCT-116 cells and does not promote the growth and proliferation of cancer cells. Upon close analysis of FIGS. 11A-11B, no indication was observed in mass death of both cell lines which confirmed that CoMnRFe@BTO (R=Ce, Eu, Tb, Tm, and Gd) MENs may not be toxic. FIG. 11A shows cell viability of HEK-293 and FIG. 11B shows cell viability of HCT-116 cell lines using MTT assay. The BTO is the most promising nanomaterial with huge potential in a wide range of nanomedicine applications. Owing to its good biocompatibility, protectivity and its applicability in multifunctional theragnostic devices including drug delivery, cell stimulation, and tissue engineering. Therefore, it was expected that the BTO coated each core composite and isolated its harm effects from the cells. In addition, the cytotoxicity examination of core CoMnRFe (R=Ce, Eu, Tb, Tm, and Gd) on the normal non-cancerous cells has proven its safety in case of any decomposition of the BTO shell in the cells will not be significantly affected and remain intact. On the other hand, the core CoMnRFe (R=Tm and Gd) has proven its toxicity on cancerous cells (HCT-116) when coated with the BTO and loaded with anti-cancer drug it might exhibited a synergic toxic effect toward the cancerous cells. These findings stress the biocompatibility and safely using of the BTO coating core-shell MENs as drug nanocarrier in vitro.

Figure 12A:
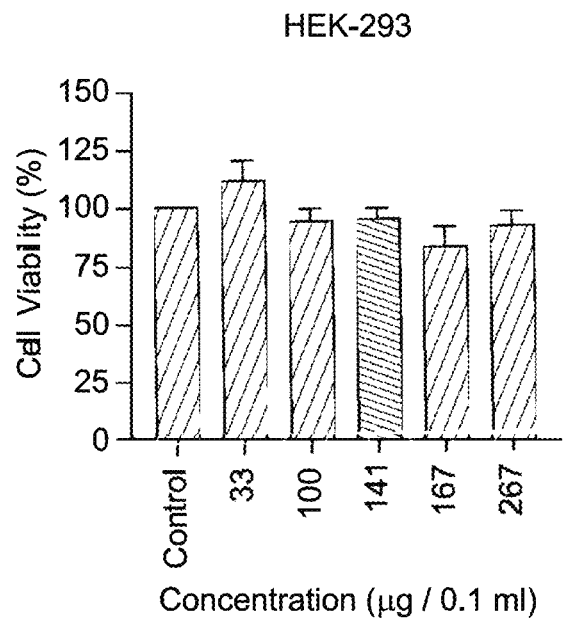
FIGS. 12A-12B illustrate the cell viability of the HEK-293 cell lines, and HCT-116 cell lines using MTT assay with various core-shell composites CoMnRFe@BTO (R=Ce, Eu, Tb, Tm and Gd), at various concentrations, according to certain embodiments.
Figure 12B:
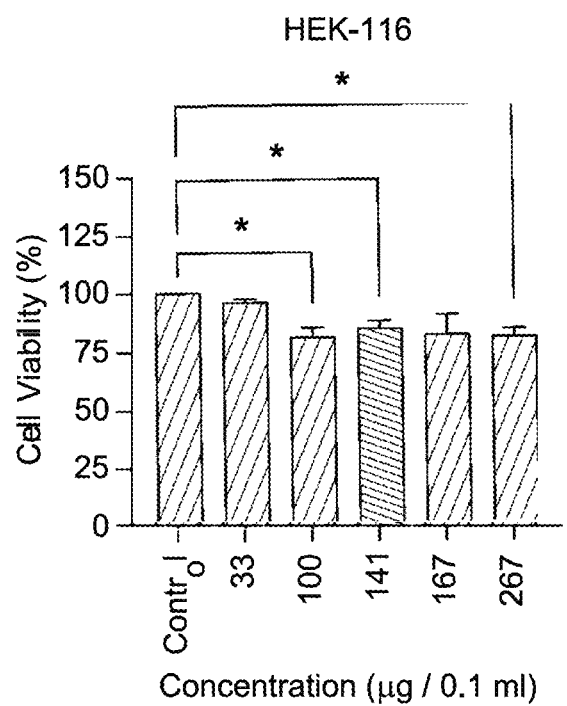

The average treatment concentration of CoMnRFe@BTO MENs was determined to be around 141.75 μg/0.1 ml and compared to the original concentrations as illustrated in FIGS. 12A-12B. A significant reduction in HCT-116 cell viability (FIG. 12B) was observed in comparison with normal HEK-293 cells while sparing normal ones at the concentrations of (100, 141.75, and 267 μg/0.1 ml) (FIG. 12A). The selective property where the piezoelectric nanomaterials (such as barium titanate) induced ultrasound that can generate electrical charges weaken functions of breast cancer cells. The results indicate that in addition to its protective effect, CoMnRFe@BTO MENs possess a dual functionality (nano-carrier and anti-cancer activity) at the aforementioned concentrations.

Nanoparticle's (NPs) composite of shell barium titanate core-gold was reported for hyperthermia therapy. These nanocomposite own a core-shell framework since the external face atoms vary from those atoms located in the core of the framework that make different biological properties between the effect of core and the core-shell with specific properties such as higher chemical and thermal stability, functionality, and potential diversity of the core's NPs. Different designs of core-shell nanocomposites may lead to potential tuning and controlling the release of NPs of the core that can either used as drug or drug-carrier to minimize utilization of expensive materials. The nanoparticles have a unique feature against colorectal cancer in many routes such as directed delivery of fluorouracil (5-FU) to the area of colorectal cancer's area directly or orally as it tolerated against stomach digestion, and in bioimaging tumor of the colorectum region.

The system was also applied in mice for targeted delivery for treating colorectal cancer by loading it with more than 90% of maytansine derivative drug. The inhibitory concentration ($IC_{50}$) values of CoMnRFe@BTO MEN was calculated. The $IC_{50}$ values were in the range of 161.86 μg/0.1 ml to 216.73/0.1 ml for HCT-116 cells. In addition, the impact of CoMnRFe@BTO MENs on normal and non-cancerous cells (HEK-23) were examined. The $IC_{50}$ values were in the range of 185.16 μg/0.1 ml to 245.63/0.1 ml. It was observed that CoMnRFe@BTO MENs caused inhibitory effects on the HEK-293 cells, but their inhibitory effects were lesser compared to colorectal cancer cells (HCT-116), which suggest that CoMnRFe@BTO MENs caused better cell death in cancer cells than normal cells.

Figures 13A, 13B, 13C:
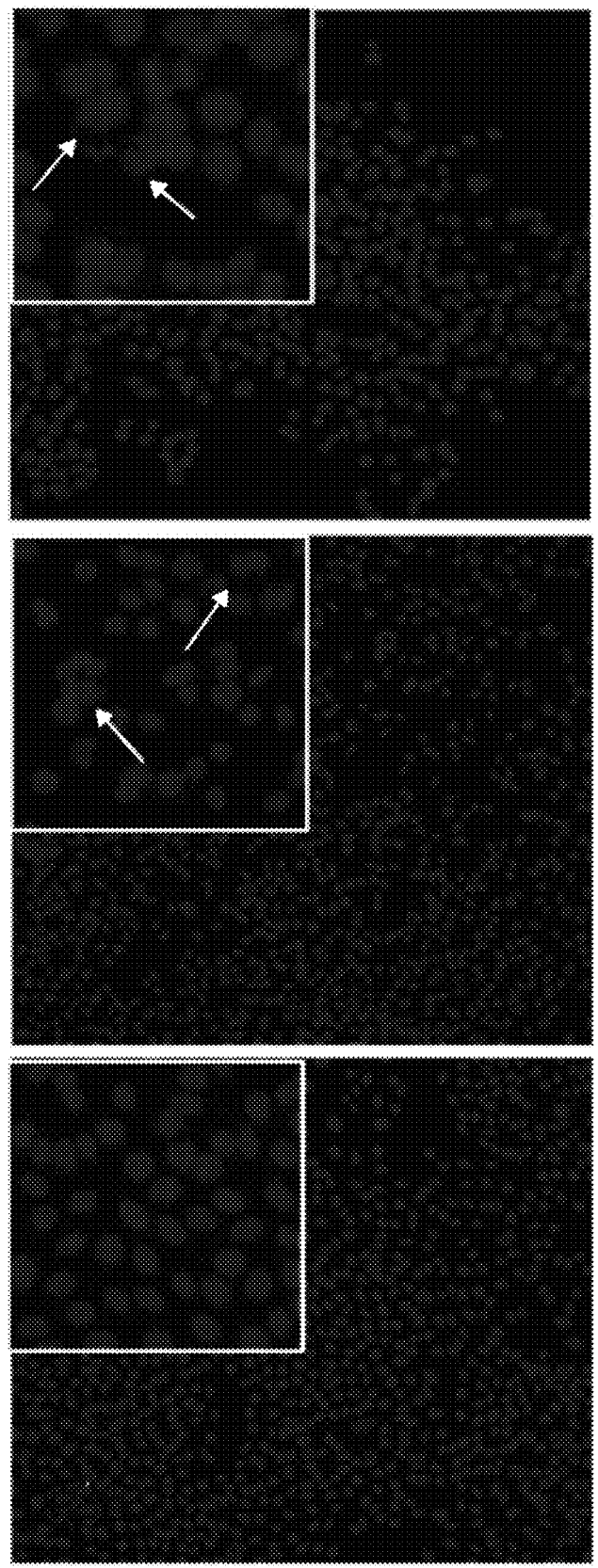
FIGS. 13A-13C illustrate impact of the core composites on colorectal cancer HCT-116 cells stained with DAPI post 48-hour treatment, according to certain embodiments.
Figures 14A, 14B, 14C:
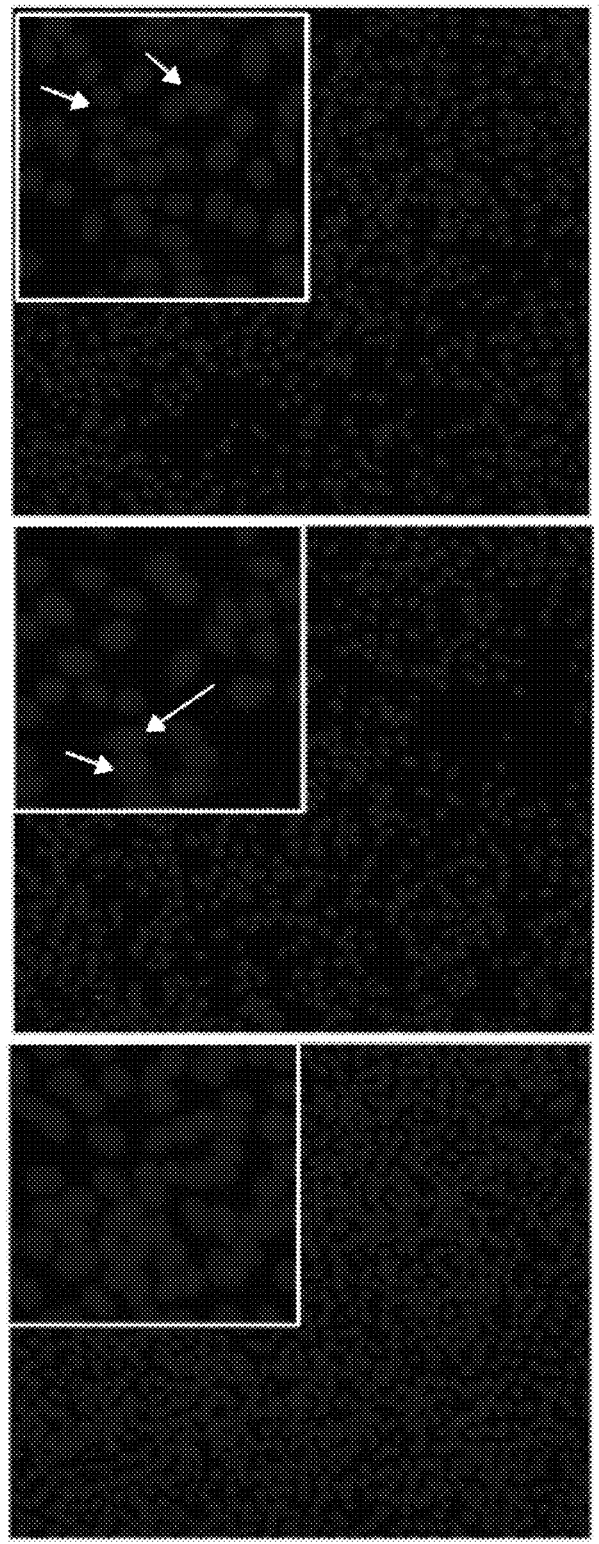
FIGS. 14A-14C illustrate impact of the MENs treatment with a) control cells, b) CoMnTmFe@BTO, and c) CoMnGdFe@BTO, respectively, on the HCT-116 cells stained with DAPI post 48 h according to certain embodiments.

The DAPI has been used to examine the cancer cell DNA after the treatment. DAPI is a fluorescent stain that binds strongly to A-T-rich regions in DNA. DAPI is a blue-fluorescent DNA stain that exhibits ~20-fold enhancement of fluorescence upon binding to AT regions of dsDNA. Because of its high affinity for DNA, it is also frequently used for counting cells, measuring apoptosis, sorting cells based on DNA content, and as a nuclear segmentation tool in high-content imaging analysis. DAPI has been extensively used as the marker for apoptotic cell death. DAPI staining was performed for visualization the apoptosis signs include condensation and fragmentation of nuclei after treatments of core CoMnRFe NPs. The CoMnTmFe and CoMnGdFe treated DAPI-stained cells showed an inhibitory action on colon cancer cells (FIGS. 13B and 13C) compared to control cells (FIG. 13A). The nuclear condensation and fragmentation were observed in the nanocomposites treated cancer cells as revealed by DAPI nuclear staining. In addition, it was also observed as a clear increase in nuclear condensation, cell membrane disintegration, and cell death (FIGS. 13B and 13C), which suggest that CoMnRFe (R=Tm and Gd) induced cell death through the apoptotic pathway (proapoptotic effect). The treatment of CoMnRFe@BTO (R=Tm and Gd) also caused minor cell death as revealed by DAPI stained cells as seen in (FIGS. 14B and 14C). These findings co-related with the MTT cytotoxicity results.

Various core CoMnRFe and core-shell CoMnRFe@BTO (R=Ce, Eu, Gd, Tb, and Tm) MENs were prepared for use in colorectal cancer therapy. Structural, morphological, and magnetoelectric analyses of the core-shell CoMnRFe@BTO (R=Ce, Eu, Gd, Tb, and Tm) confirmed the formation of the core-shell MENs. The MENs with different compositions confirm the coexistence of both phases' spinel ferrites and the BTO. The lattices parameters fluctuated with changing the type of the dopant in CoMnRFe (R=Ce, Eu, Gd, Tb, and Tm), wherein the nanocrystalline sizes ranged from 27 to 41 nm. The morphology analysis by SEM showed that the core-shell MENs revealed an aggregation of spherical grains. The ME coupling revealed that CoMnRFe@BaTiO$_3$ MENs showed the maximum value of $\alpha_{ME}$=24.9 mV/cm·Oe at H$_{DC}$~1800 Oe. The impact of prepared CoMnRFe NPs and CoMnRFe@BTO MENs on HCT-116 cells was evaluated, and the results were compared to normal non-cancerous cells, HEK-293, using MTT assay and DAPI Staining. After 48 h of treatment, it was observed that the core CoMnRFe NPs showed selective significant inhibitory effect p<0.05 on colon cancer (HCT-116) cells at the concentration of (141.75 μg/0.1 ml), whereas HEK-293 cells also showed inhibitory action due to CoMnRFe treatments, but the percentage of cell viability was higher than HCT-116 cells. In addition, the nuclear DNA of HCT-116 cells by DAPI staining was examined, and it was found that CoMnRFe NPs and CoMnRFe@BTO MENs induced cell death as revealed by DAPI staining. Finally, the results indicate that the CoMnRFe NPs and CoMnRFe@BTO MENs possess anti-colon cancer capabilities, but CoMnRFe@BTO MENs has an advantage over CoMnRFe NPs as it does not cause a cytotoxic effect on normal (HEK-293) cells compared to CoMnRFe NPs. Therefore, the MEN of the present disclosure, are biocompatible and effective for treating cancer.

Obviously, numerous modifications and variations of the present disclosure are possible in light of the above teachings. It is therefore to be understood that within the scope of the appended claims, the disclosure may be practiced otherwise than as specifically described herein.

The invention claimed is:

1. A method of preferentially killing cancer cells, the method comprising:
    contacting a magnetoelectric nanocomposite (MEN) and a cell culture comprising kidney (HEK)-293 cells or HCT-116 colorectal cancer cells, the MEN comprising:
        a shell comprising barium titanate; and
        a rare earth metal doped spinel ferrite nanoparticle (SFNP) core, having a formula of $$Co_{0.8}Mn_{0.2}Eu_{0.02}Fe_{1.98}O_4,$$

wherein particles of the MEN have an average crystallite size of 41.25±0.05,
    wherein upon the contacting with the MEN a higher percentage of the HCT-116 colorectal cancer cells are killed compared to the human embryonic kidney (HEK)-293, and
    wherein, in the contacting, the cell culture of the HEK-293 cells or the HCT-116 colorectal cancer cells are contacted with the MEN in a range of from greater than 330 to less than 1410 g/mL for 48 hours.

2. The method of claim 1, wherein the particles of the MEN have a substantially spherical shape with an average size in a range of from 5 to 30 nm, and
    wherein the spheres are agglomerated to form aggregates with an average size in a range of from 50 to 500 nm.

3. The method of claim 2, wherein the MEN comprises: 27-33 wt % Ba, 10-12 wt % Ti, 5-15 wt % Co, 3-6 wt % Mn, 0.5-1 wt % Eu, 21-25 wt % Fe, and 18-24 wt % O, based on the total weight of the Ba, Ti, Co, Mn, Eu, Fe, and O in the MEN.

4. The method of claim 3, wherein the MEN hash:
    a magnetoelectric coefficient of 14 mV/cm·Oe at 1800 Oe.

5. The method of claim 4, having:
    a zeta potential of −2.43 mV.

6. The method of claim 2, wherein the aggregates form an agglomerated network.

7. The method of claim 1, wherein the MEN consists of:
    a shell comprising barium titanate; and
    a rare earth metal doped spinel ferrite nanoparticle (SFNP) core, having a formula of $Co_{0.8}Mn_{0.2}Eu_{0.02}Fe_{1.9}O_4$.

* * * * *